US011660333B2

(12) United States Patent
Dhere et al.

(10) Patent No.: US 11,660,333 B2
(45) Date of Patent: May 30, 2023

(54) STABLE VACCINE COMPOSITIONS COMPRISING INTER ALIA LIVE ATTENUATED RECOMBINANT FLAVIVIRUS AND PROCESS FOR PREPARATION THEREOF

(71) Applicant: SERUM INSTITUTE OF INDIA PRIVATE LIMITED, Pune Maharashtra (IN)

(72) Inventors: Rajeev Mhalasakant Dhere, Pune Maharashtra (IN); Leena Ravindra Yeolekar, Pune Maharashtra (IN); Vinit Kumar, Pune Maharashtra (IN); Rohit Bapurav Sonar, Pune Maharashtra (IN); Sandeep Dinkar Baraskar, Pune Maharashtra (IN); Rajeev Mehla, Pune Maharashtra (IN); Shashikant Janardan Ghodekar, Pune Maharashtra (IN); Cyrus Soli Poonawalla, Pune Maharashtra (IN); Adar Cyrus Poonawalla, Pune Maharashtra (IN)

(73) Assignee: Serum Institute of India Private Limited, Pune Maharashtra (IN)

( * ) Notice: Subject to any disclaimer, the term of this patent is extended or adjusted under 35 U.S.C. 154(b) by 304 days.

(21) Appl. No.: 16/756,227

(22) PCT Filed: Oct. 10, 2018

(86) PCT No.: PCT/IN2018/050645

§ 371 (c)(1),
(2) Date: Apr. 15, 2020

(87) PCT Pub. No.: WO2019/077622

PCT Pub. Date: Apr. 25, 2019

(65) Prior Publication Data

US 2021/0187092 A1 Jun. 24, 2021

(30) Foreign Application Priority Data

Oct. 16, 2017 (IN) ............................ 201721036696

(51) Int. Cl.
*A61K 39/12* (2006.01)
*C12N 7/06* (2006.01)
*A61K 39/00* (2006.01)

(52) U.S. Cl.
CPC ................ *A61K 39/12* (2013.01); *C12N 7/06* (2013.01); *A61K 2039/5254* (2013.01);
(Continued)

(58) Field of Classification Search
None
See application file for complete search history.

(56) References Cited

U.S. PATENT DOCUMENTS

| | | | | |
|---|---|---|---|---|
| 10,751,408 | B2 * | 8/2020 | Randolph | A61K 39/12 |
| 11,123,420 | B2 * | 9/2021 | Jain | A61K 9/19 |

(Continued)

FOREIGN PATENT DOCUMENTS

| | | | |
|---|---|---|---|
| WO | 2008/118691 | A2 | 10/2008 |
| WO | 2010/036774 | A1 | 4/2010 |

(Continued)

OTHER PUBLICATIONS

Lueckel B, Bodmer D, Helk B, Leuenberger H. Formulations of sugars with amino acids or mannitol—influence of concentration ratio on the properties of the freeze-concentrate and the lyophilizate. Pharm Dev Technol. Aug. 1998;3(3):325-36. (Year: 1998).*

*Primary Examiner* — Michelle S Horning
(74) *Attorney, Agent, or Firm* — BakerHostetler; Tayan B. Patel

(57) ABSTRACT

Stable lyophilized immunogenic compositions include inter alia live attenuated recombinant flaviviruses, more preferably live attenuated recombinant dengue viruses, at least one carbohydrate, at least one amino acid and is particularly amenable to rapid freeze-drying treatments wherein, the composition preserves desired characteristics of a virus,
(Continued)

RNA sequence of dengue virus strains including virus viability, immunogenicity and stability. The immunogenic composition is devoid of preservatives, polymers and surfactants. The methods for manufacturing the stable lyophilized immunogenic compositions are also provided.

21 Claims, 15 Drawing Sheets

(52) U.S. Cl.
CPC ............... *A61K 2039/55505* (2013.01); *A61K 2039/55561* (2013.01); *A61K 2039/55566* (2013.01); *A61K 2039/55572* (2013.01); *A61K 2039/55577* (2013.01); *A61K 2039/55583* (2013.01); *C12N 2770/24134* (2013.01)

(56) References Cited

U.S. PATENT DOCUMENTS

| | | | |
|---|---|---|---|
| 2010/0015180 | A1 | 1/2010 | Francon et al. |
| 2012/0141528 | A1 | 6/2012 | Coffey et al. |
| 2015/0030565 | A1 | 1/2015 | Mundle et al. |

FOREIGN PATENT DOCUMENTS

| | | | |
|---|---|---|---|
| WO | 2010/146598 | A2 | 12/2010 |
| WO | 2017/041156 | A1 | 3/2017 |
| WO | 2017/056101 | A1 | 4/2017 |

* cited by examiner

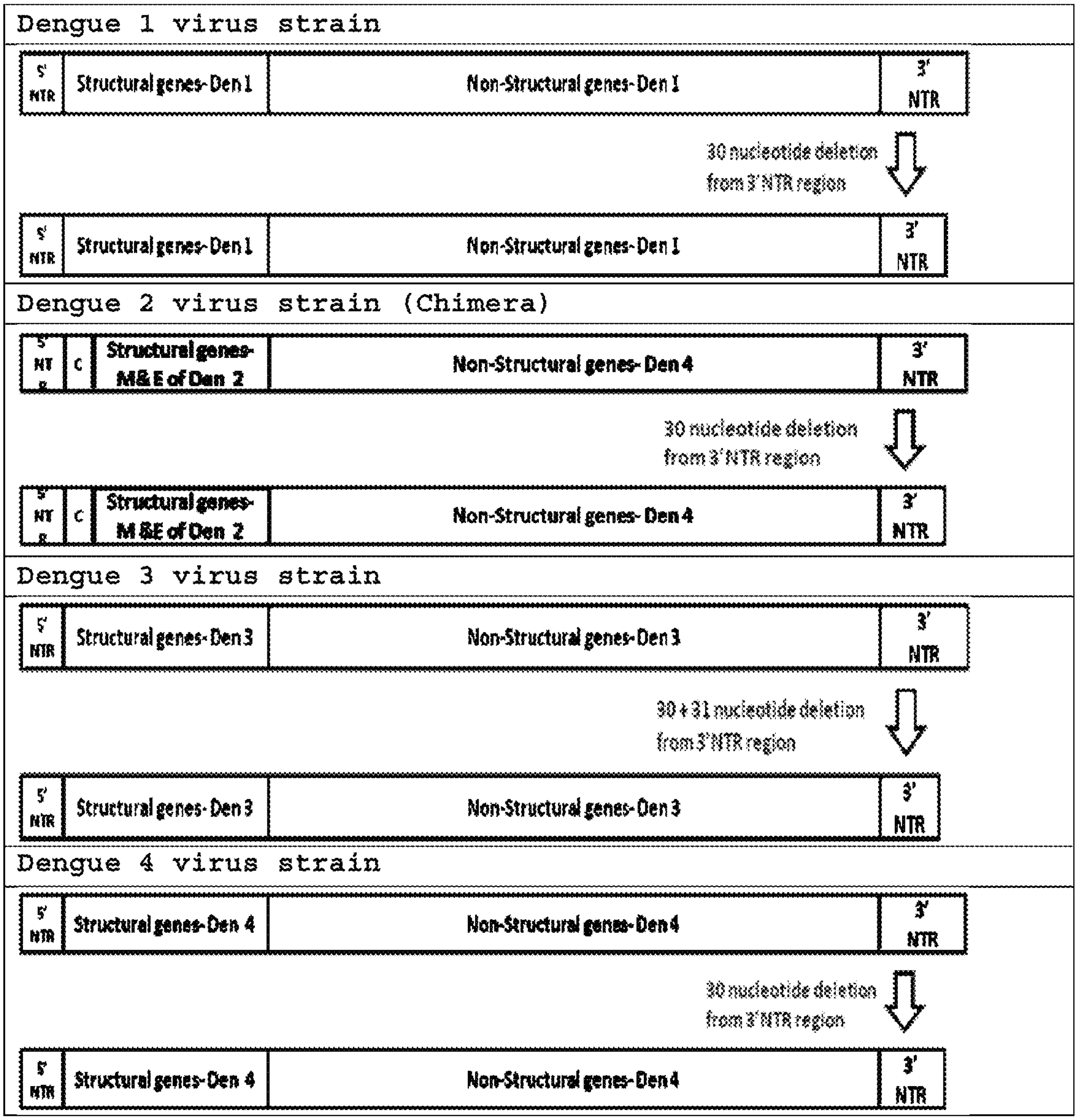
Figure 1: RNA sequence of dengue virus strains

Figure 2: Dengue virus virion structure
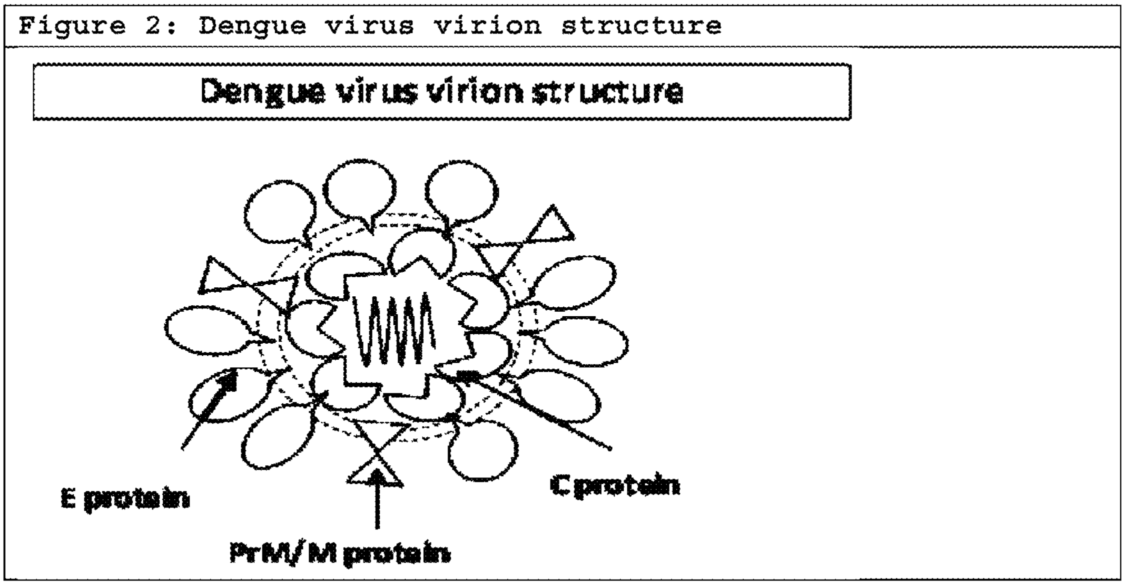
Figure 3: Dengue virion Strains structure
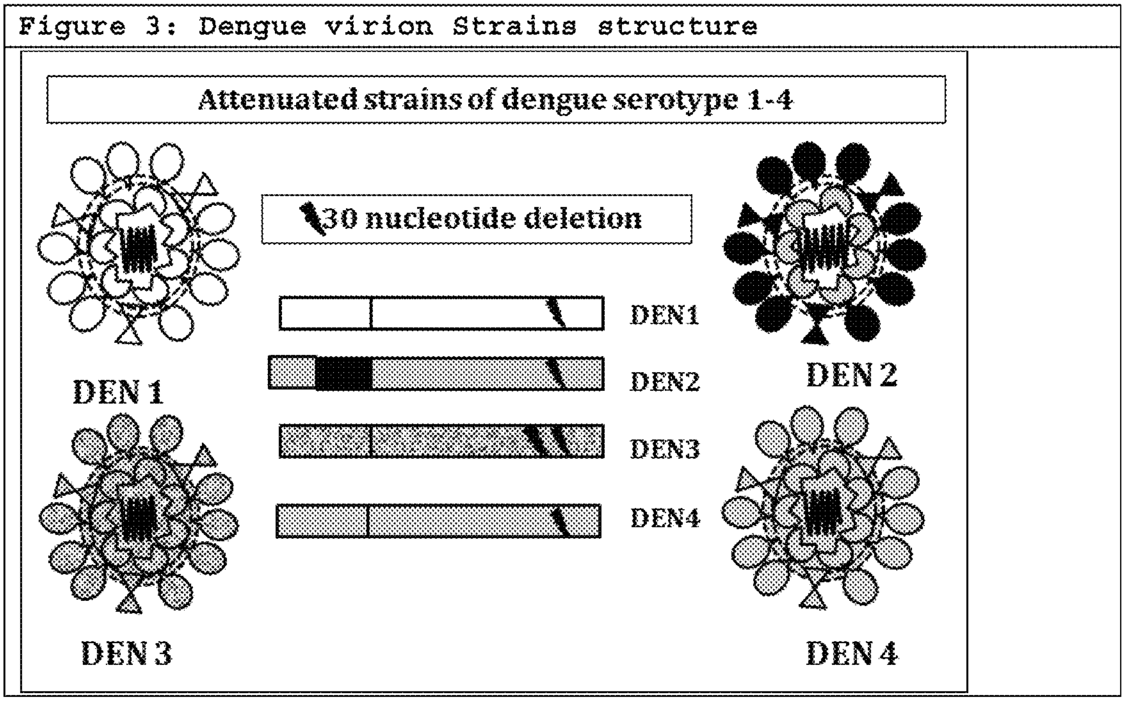

Figure 4: DEN 1 Virus Log Yield Titers ($CCID_{50}$/ml) (Multiple Harvest vs. Single Harvest)
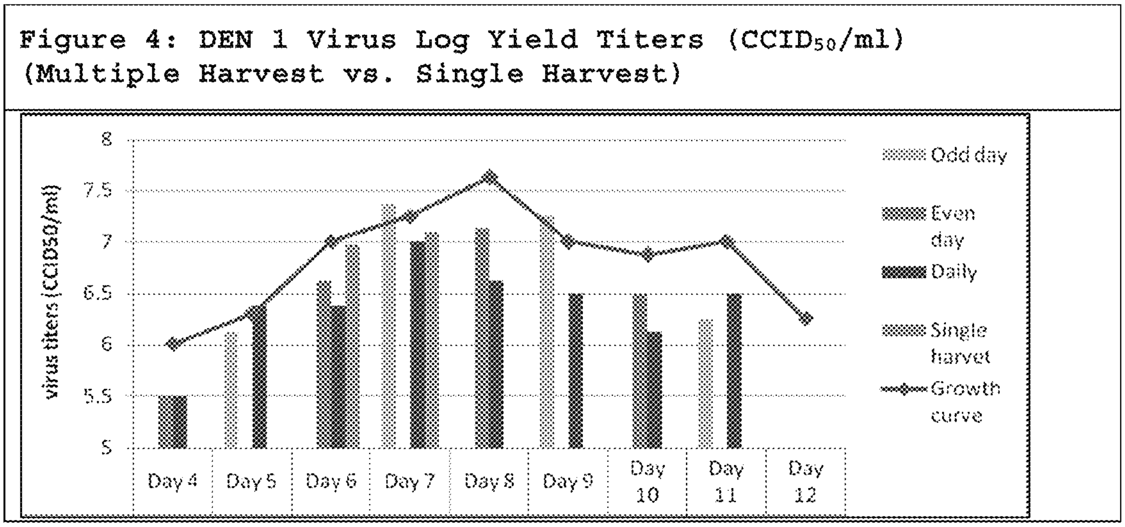
Figure 5: DEN 2, 3, 4 Virus Log Yield Titers ($CCID_{50}$/ml) (Multiple Harvest vs. Single Harvest)
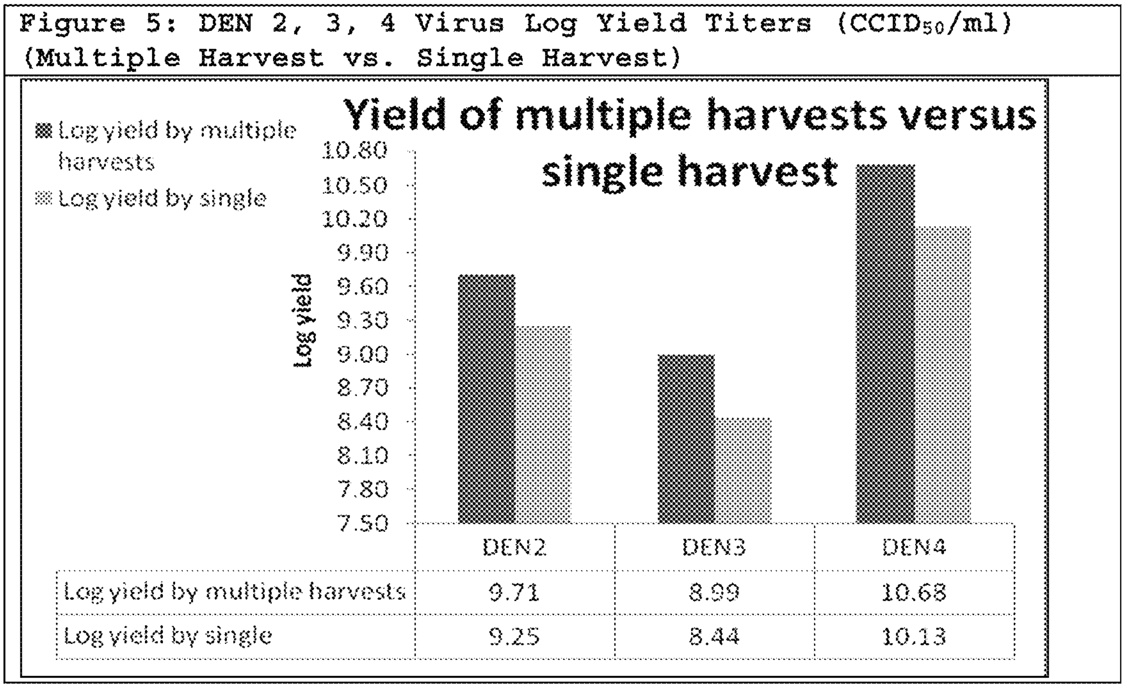
| | DEN2 | DEN3 | DEN4 |
|---|---|---|---|
| Log yield by multiple harvests | 9.71 | 8.99 | 10.68 |
| Log yield by single | 9.25 | 8.44 | 10.13 |

Figure 6: Effect of Benzonase concentration on DNA content
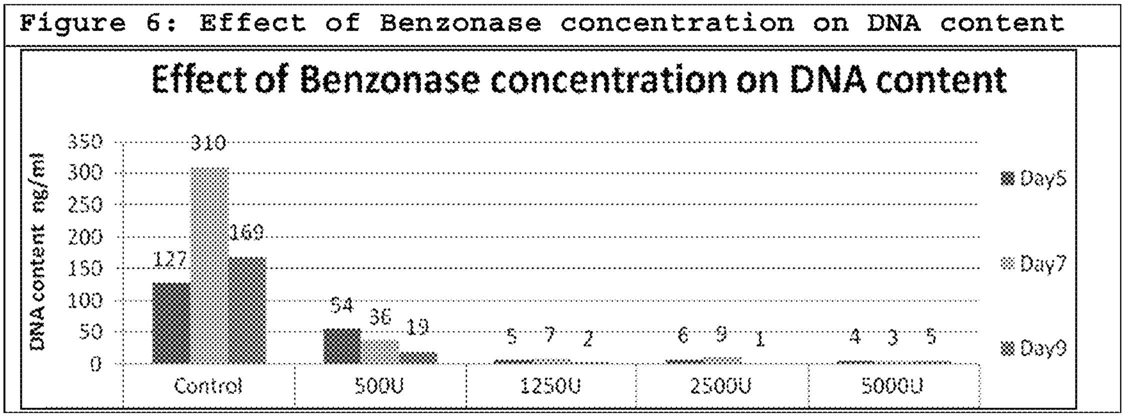
Figure 7: Effect of temperature on Cellular DNA content and virus titer
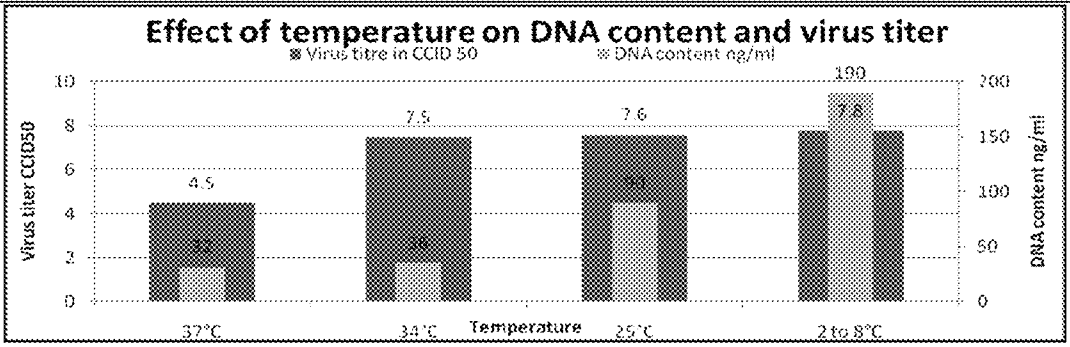
Figure 8: DEN-1 titer $CCID_{50}$/ml (Liquid vs. Lyophilized)
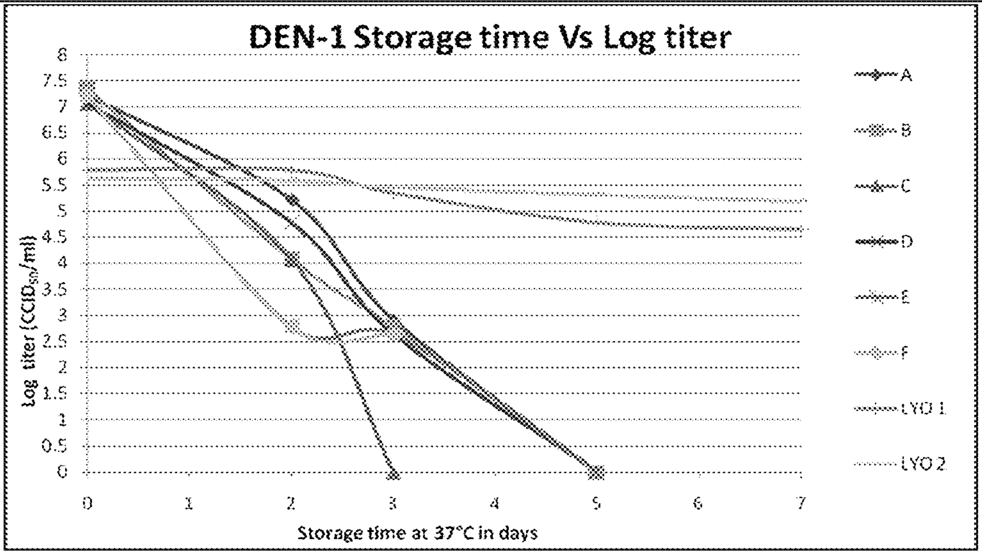

Figure 9: DEN 2 Titer $CCID_{50}$/ml (Liquid vs. Lyophilized)
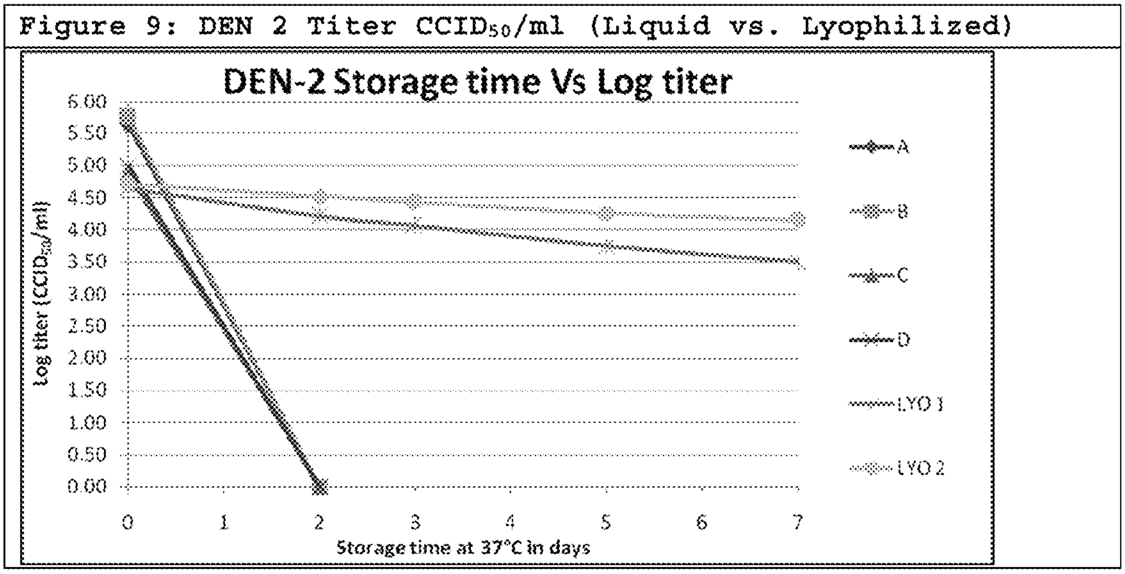
Figure 10: DEN 3 Titer $CCID_{50}$/ml (Liquid vs. Lyophilized)
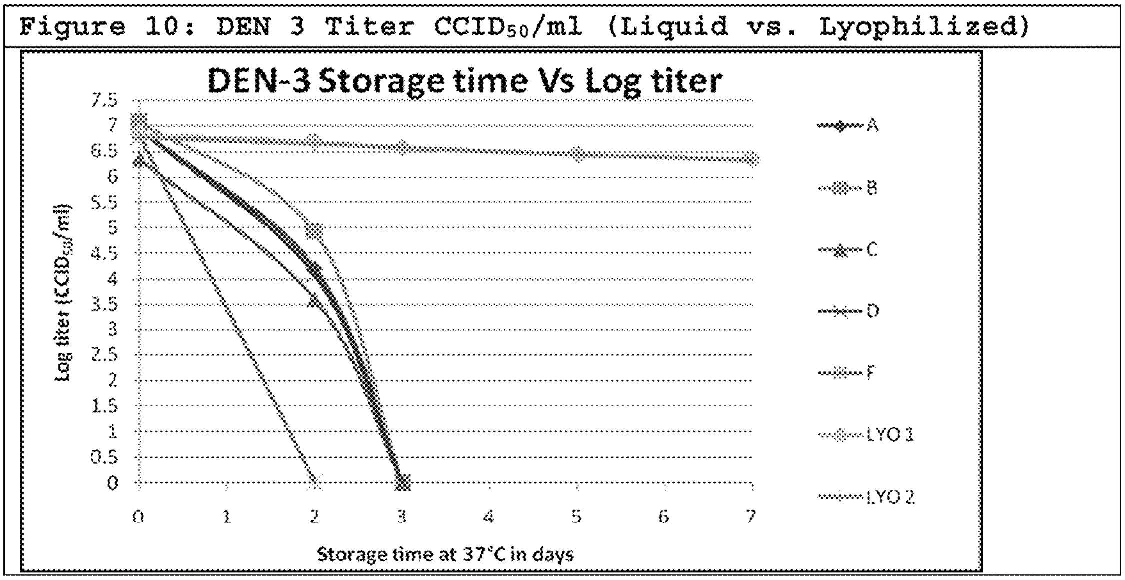

Figure 11: DEN 4 Titer $CCID_{50}$/ml (Lyophilized)
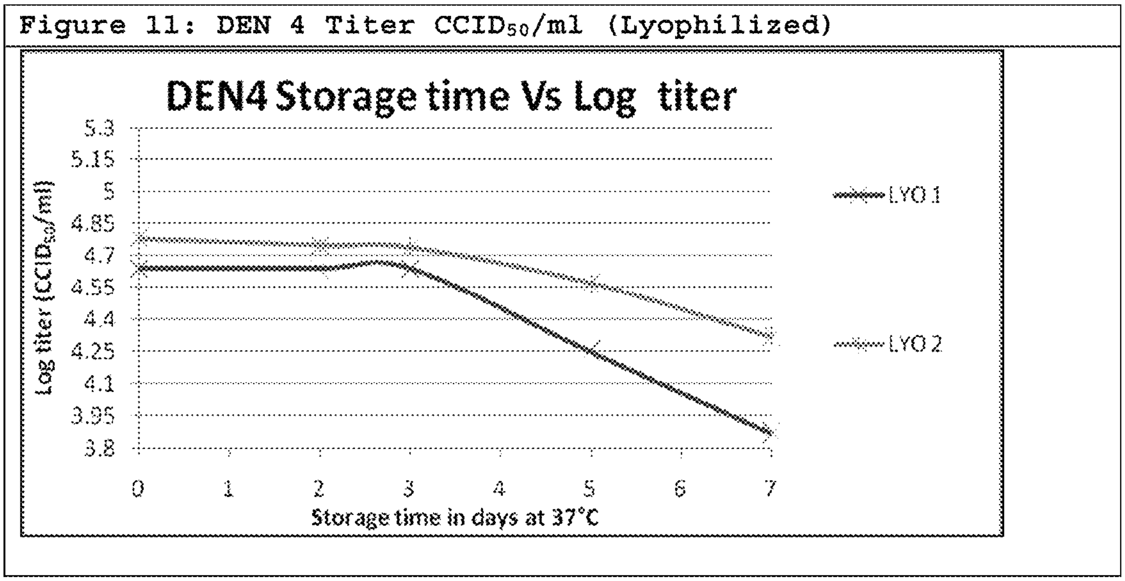
Figure 12: Lyophilization Cycle
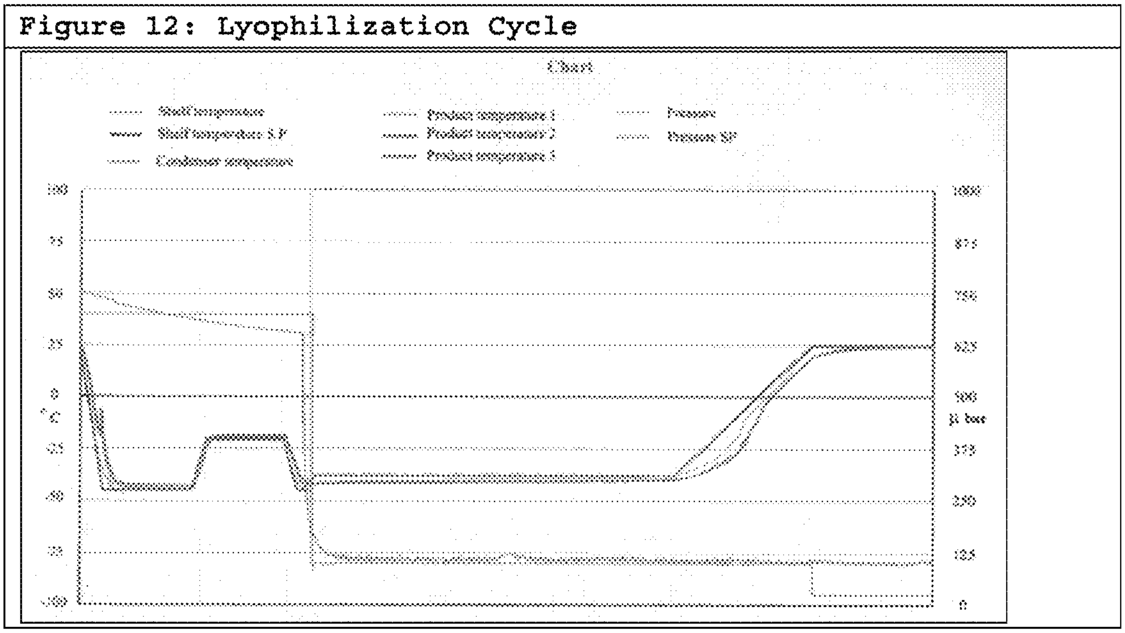

Figure 13: DEN 1 Titer $Log_{10}$ pfu/ml post lyophilization
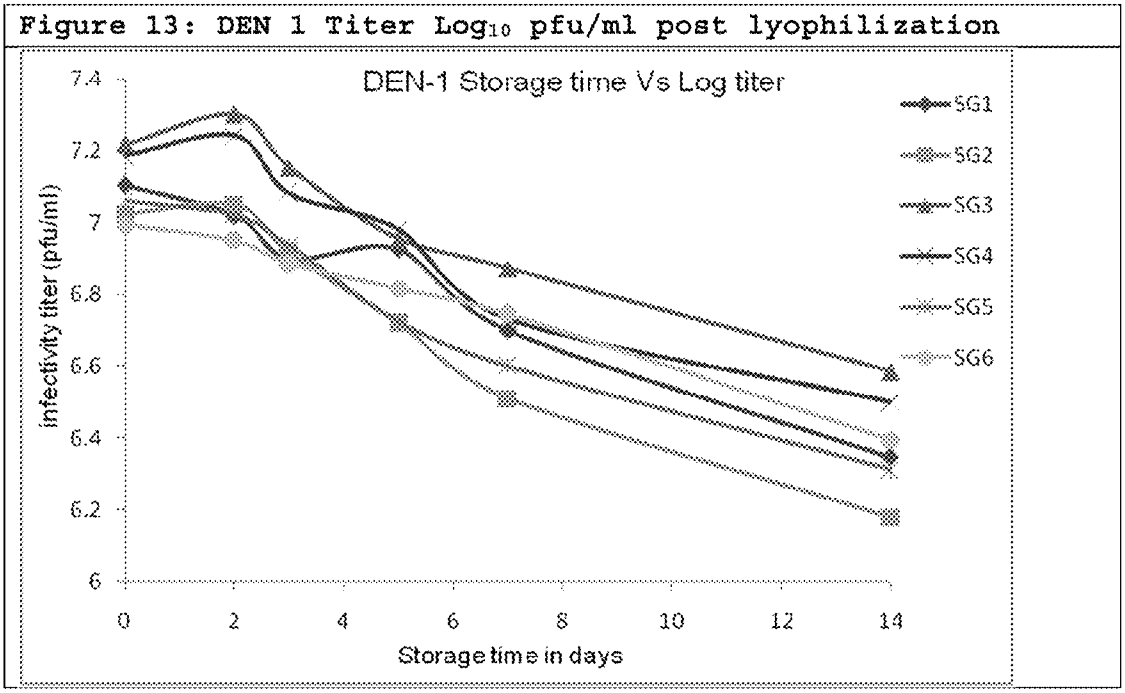
Figure 14: DEN-2 titer $Log_{10}$ pfu/ml post lyophilization
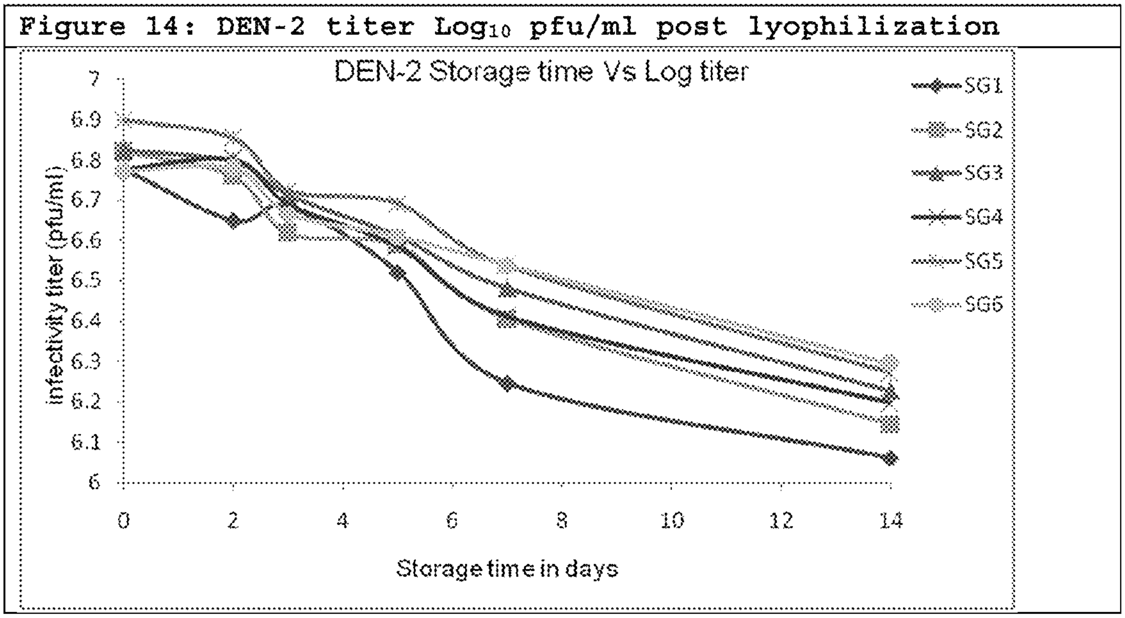

Figure 15: DEN-3 titer $Log_{10}$ pfu/ml post lyophilization
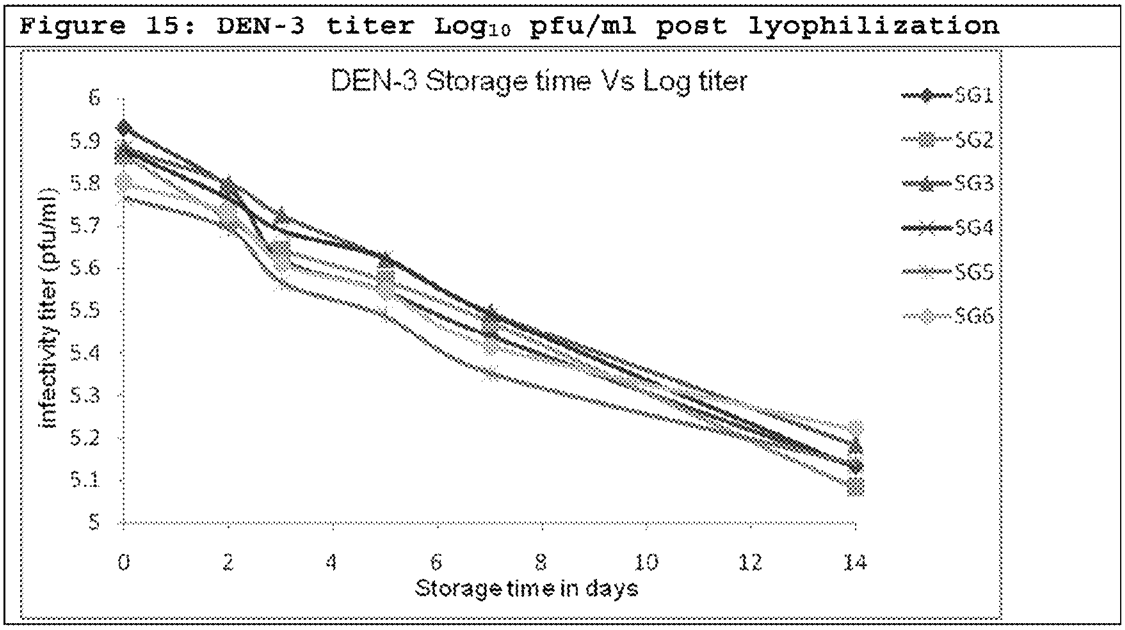
Figure 16: DEN-4 titer $Log_{10}$ pfu/ml post lyophilization
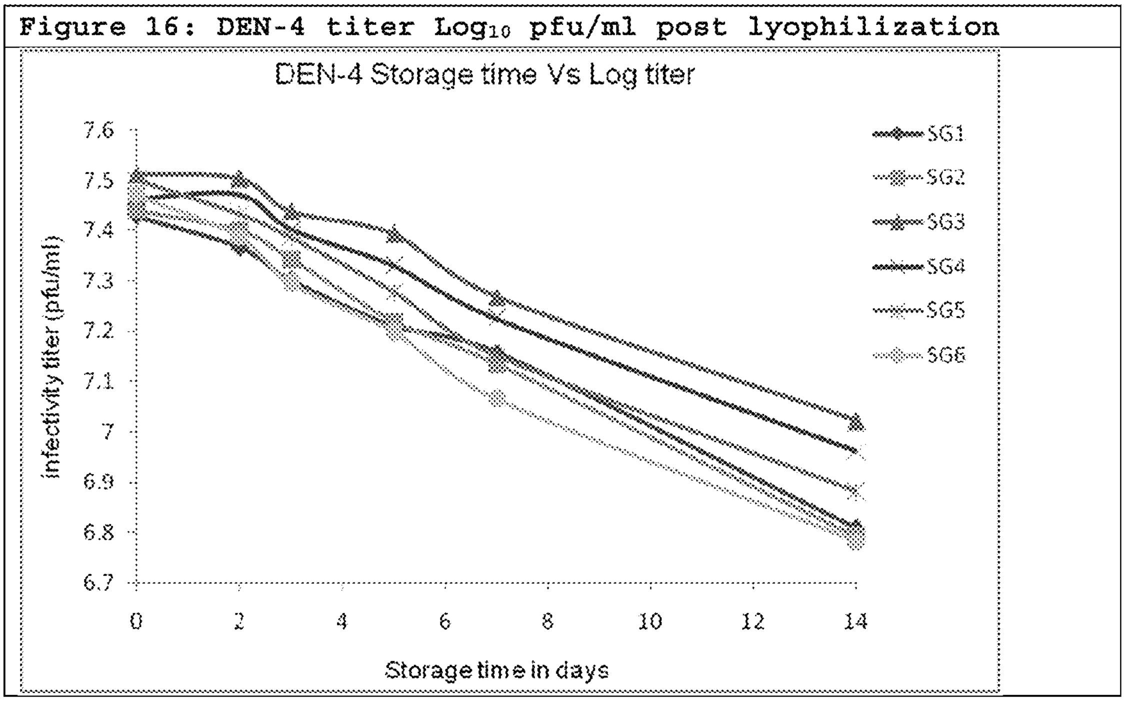

Figure 17A: DEN-1 titer $Log_{10}$ pfu/0.5 ml data post lyophilization at 2-8°C upto 12 months
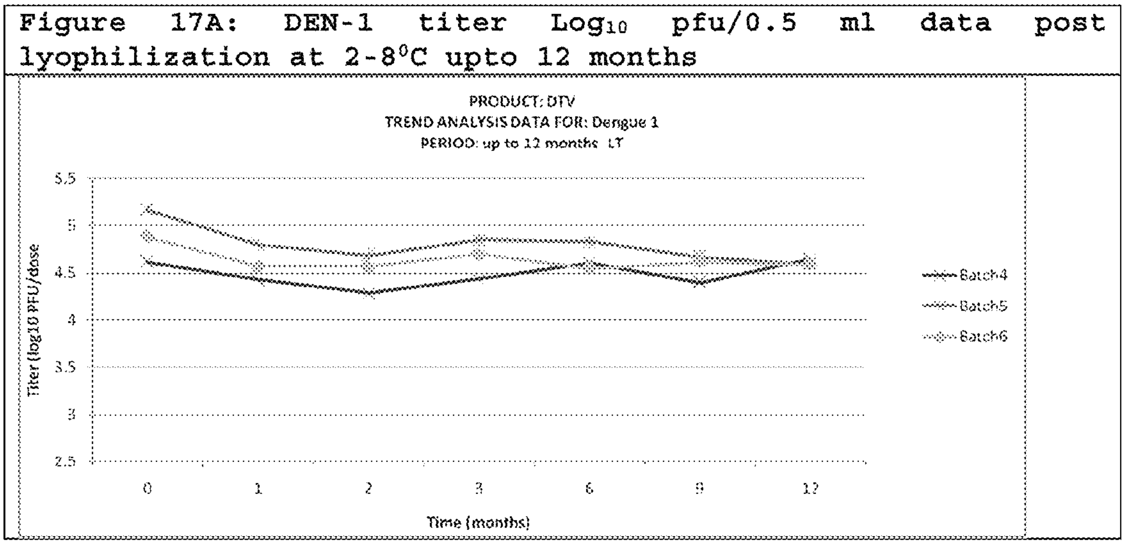
Figure 17B: DEN-2 titer $Log_{10}$ pfu/0.5 ml data post lyophilization at 2-8°C upto 12 months
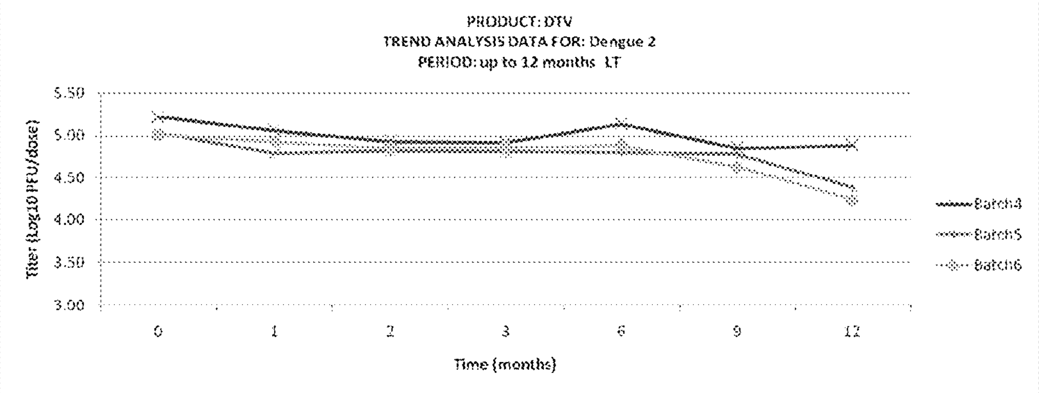

Figure 17C: DEN-3 titer $Log_{10}$ pfu/0.5 ml data post lyophilization at 2-8°C upto 12 months
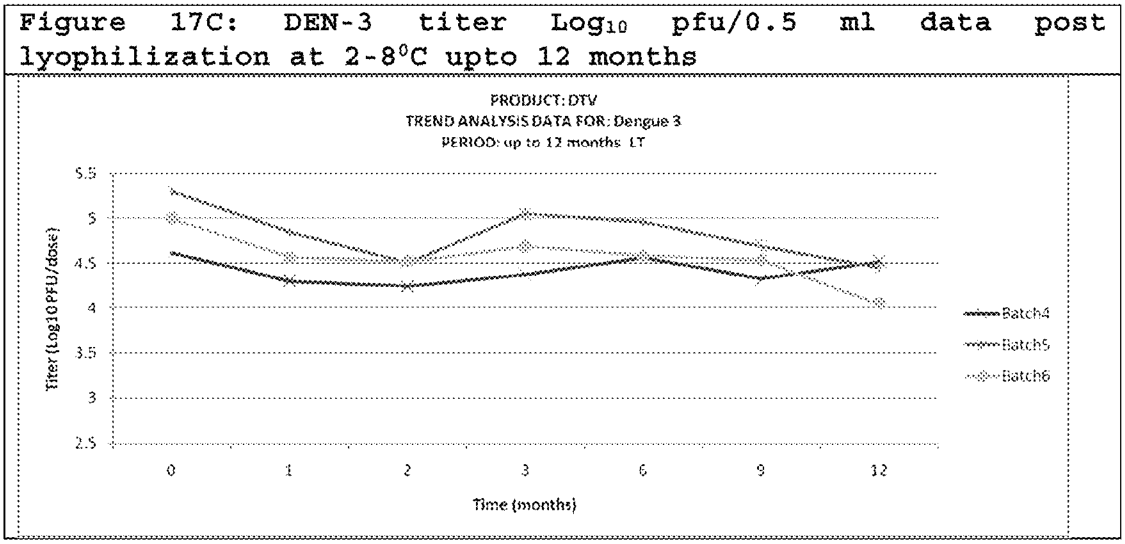
Figure 17D: DEN-4 titer $Log_{10}$ pfu/0.5 ml data post lyophilization at 2-8°C upto 12 months
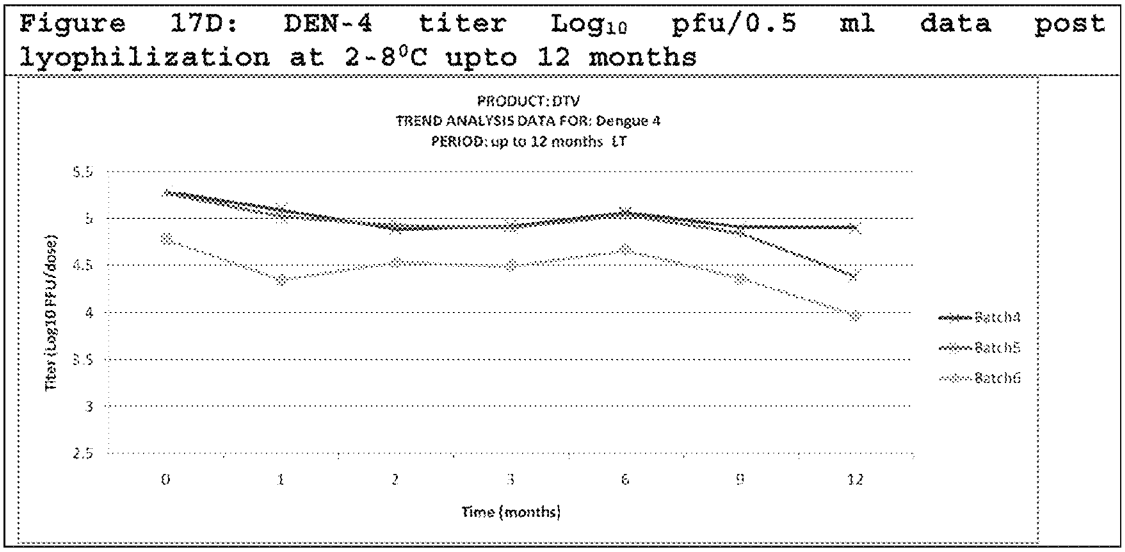

Figure 18: Dengue Tetravalent vaccine pH data post lyophilization at 2-8°C upto 12 months
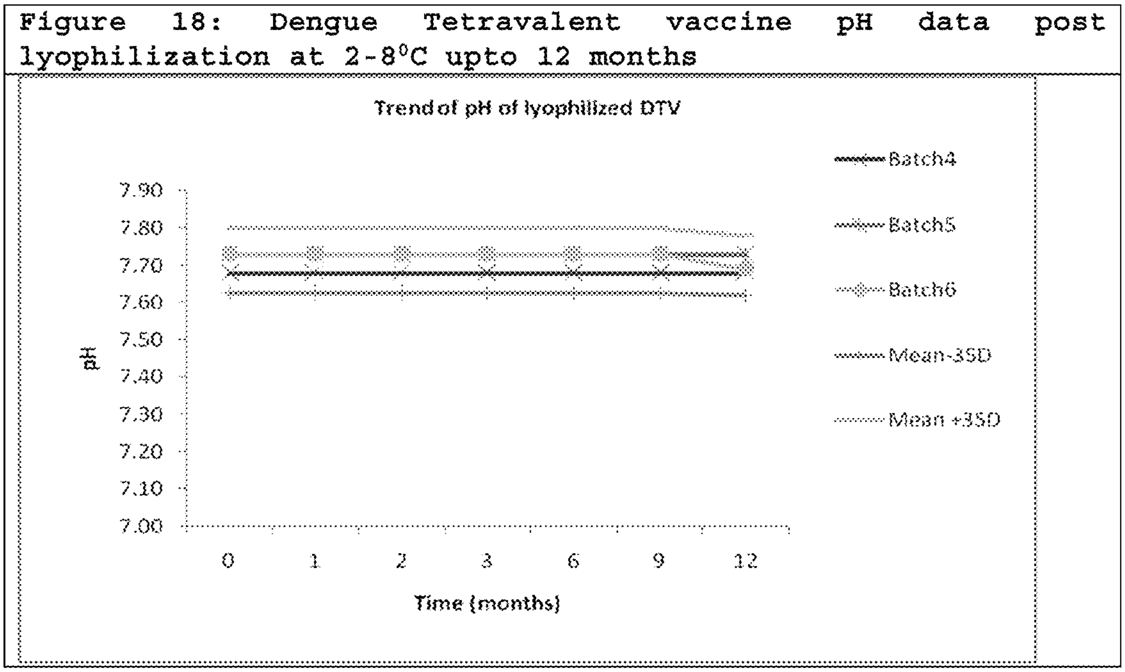
Figure 19: Dengue Tetravalent vaccine Residual Moisture data post lyophilization at 2-8°C upto 12 months
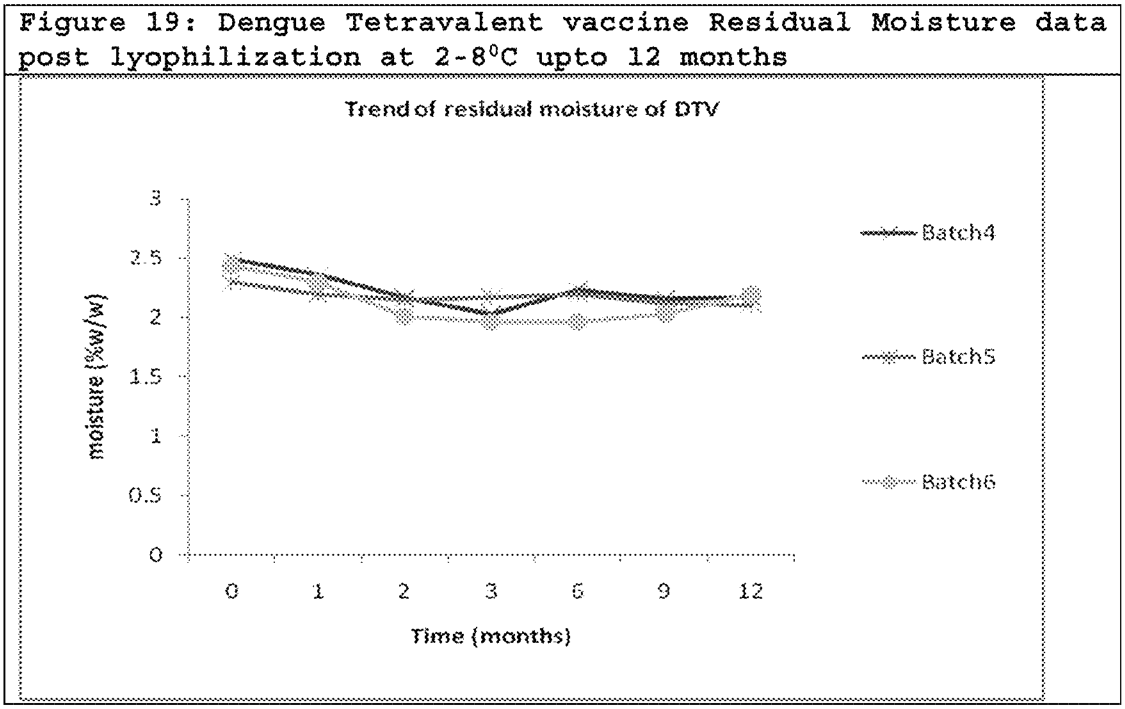

Figure 20A: DEN-1 titer $Log_{10}$ pfu/0.5 ml data post lyophilization at 25°C±2°C upto 6 months
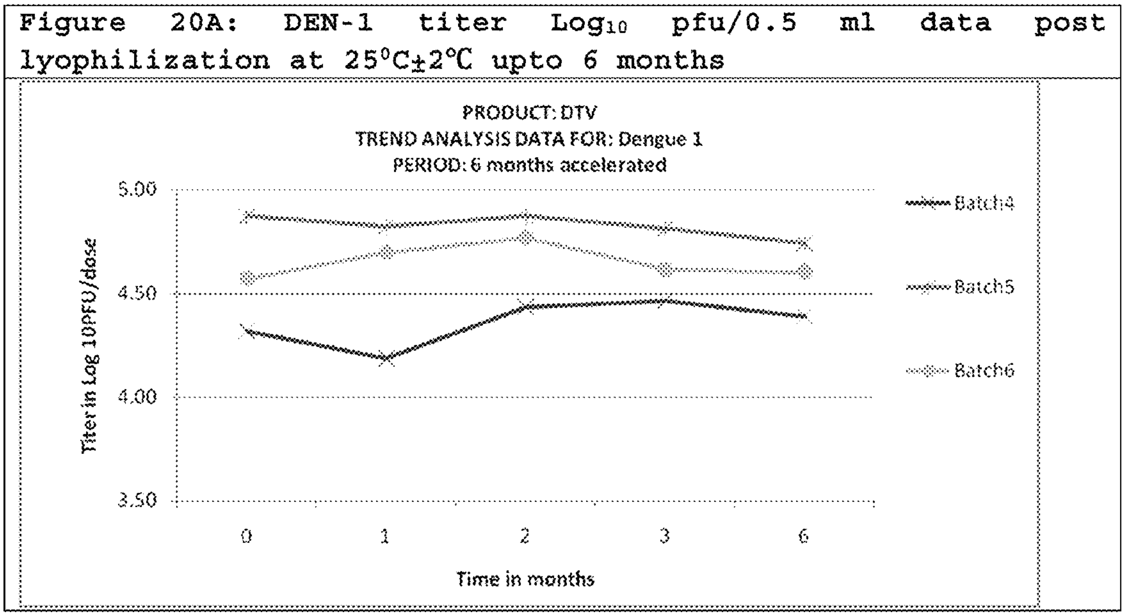
Figure 20B: DEN-2 titer $Log_{10}$ pfu/0.5 ml data post lyophilization at 25°C±2°C upto 6 months
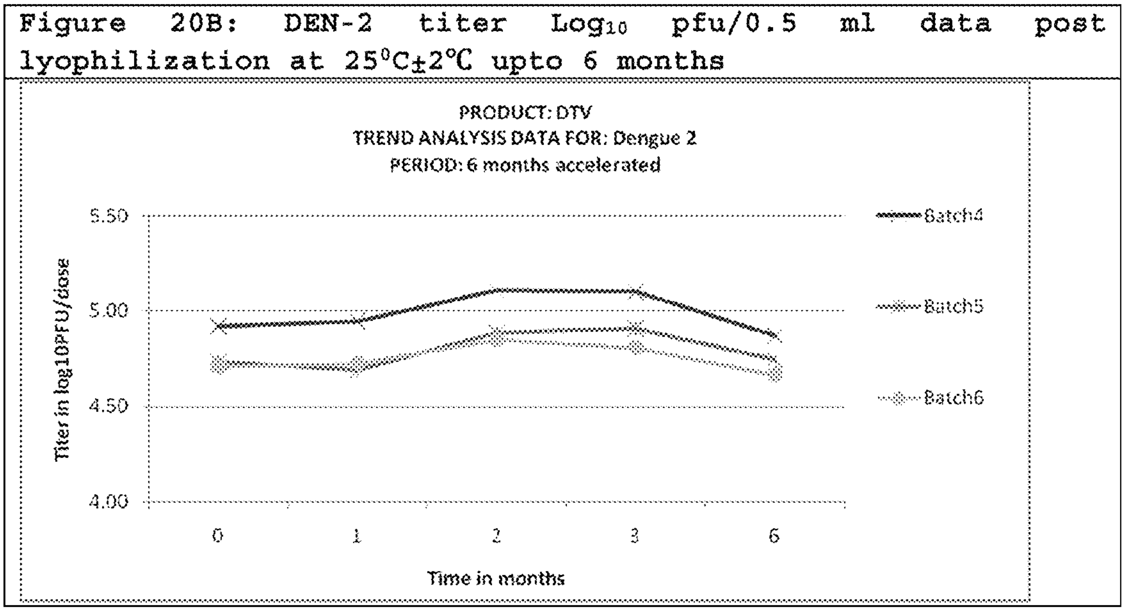

Figure 20C: DEN-3 titer $Log_{10}$ pfu/0.5 ml data post lyophilization at 25°C±2°C upto 6 months
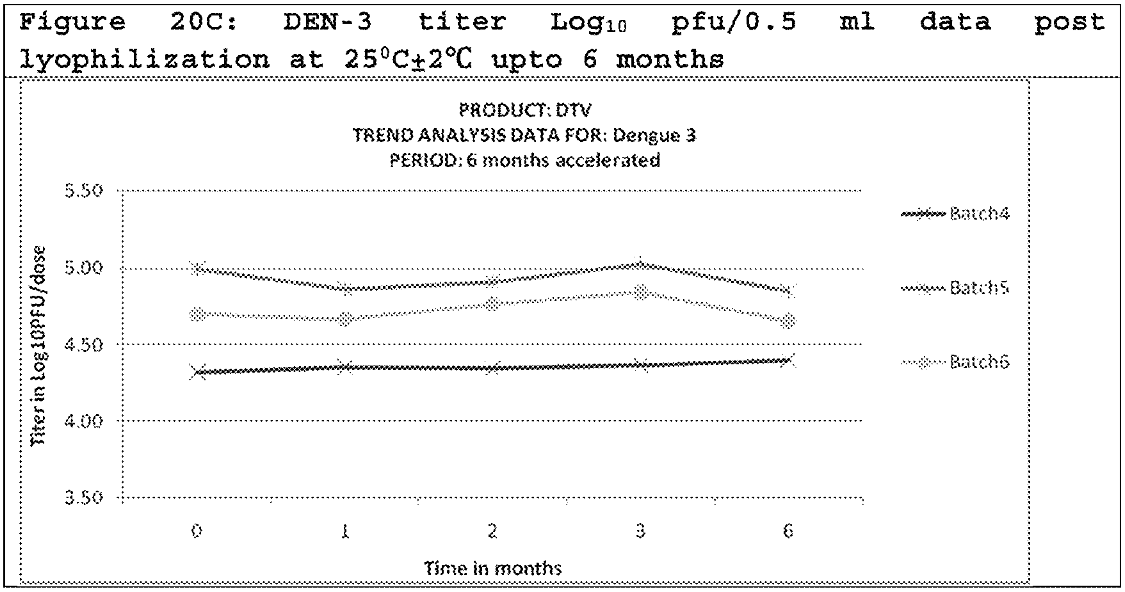
Figure 20D: DEN-4 titer $Log_{10}$ pfu/0.5 ml data post lyophilization at 25°C±2°C upto 6 months
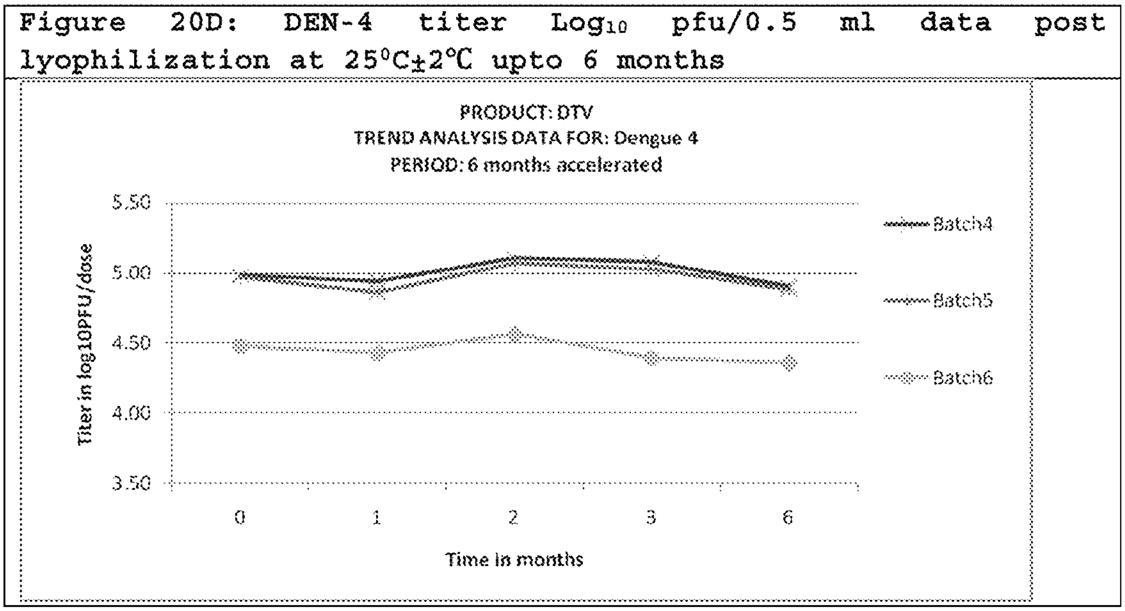

Figure 21: Dengue Tetravalent vaccine pH data post lyophilization at 25°C±2°C upto 6 months
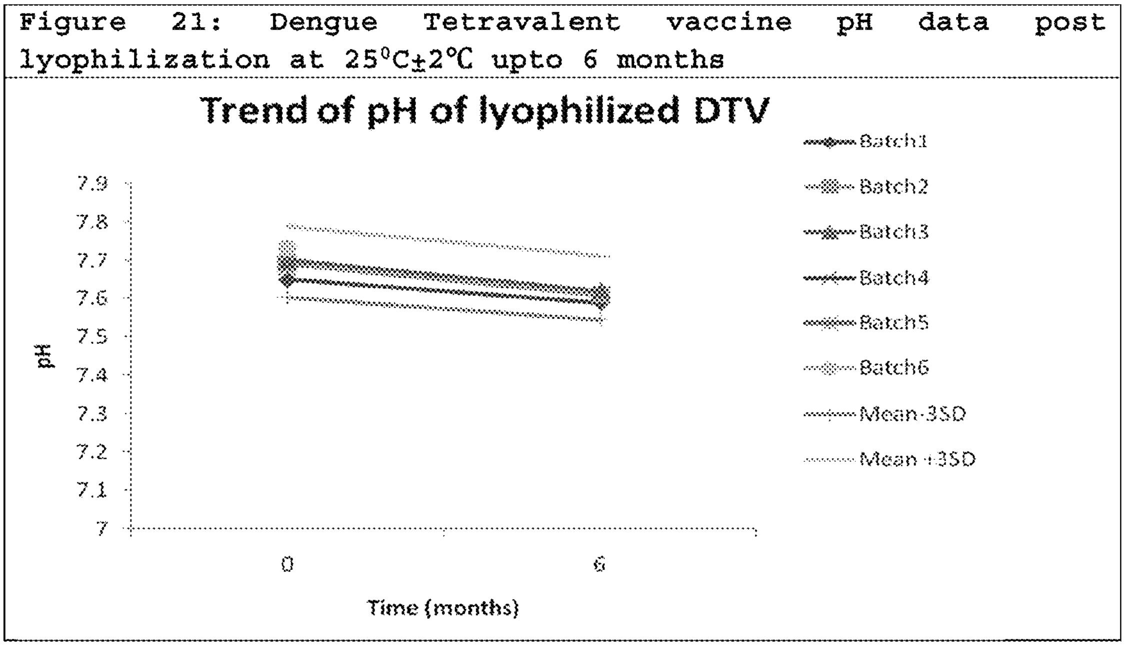
Figure 22: Dengue Tetravalent vaccine Residual Moisture data post lyophilization at 25°C±2°C upto 6 months
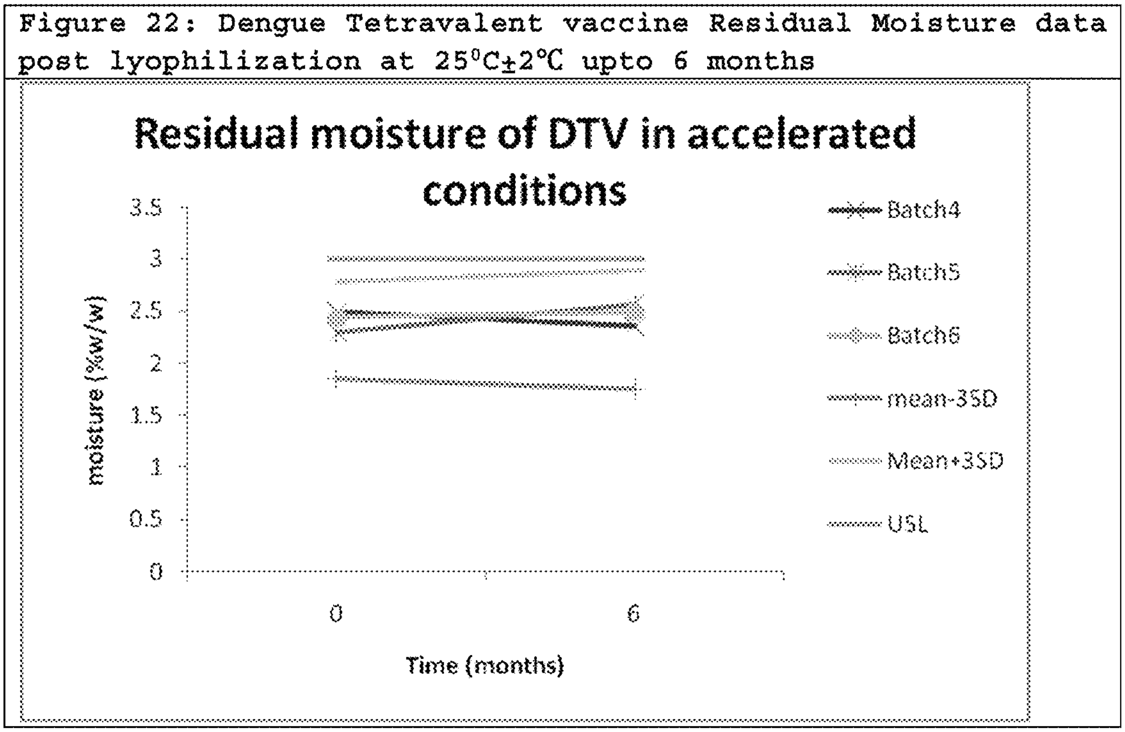

Figure 23: Dengue Tetravalent Vaccine Stability data at 37°C±1°Cupto 7 days post lyophilization
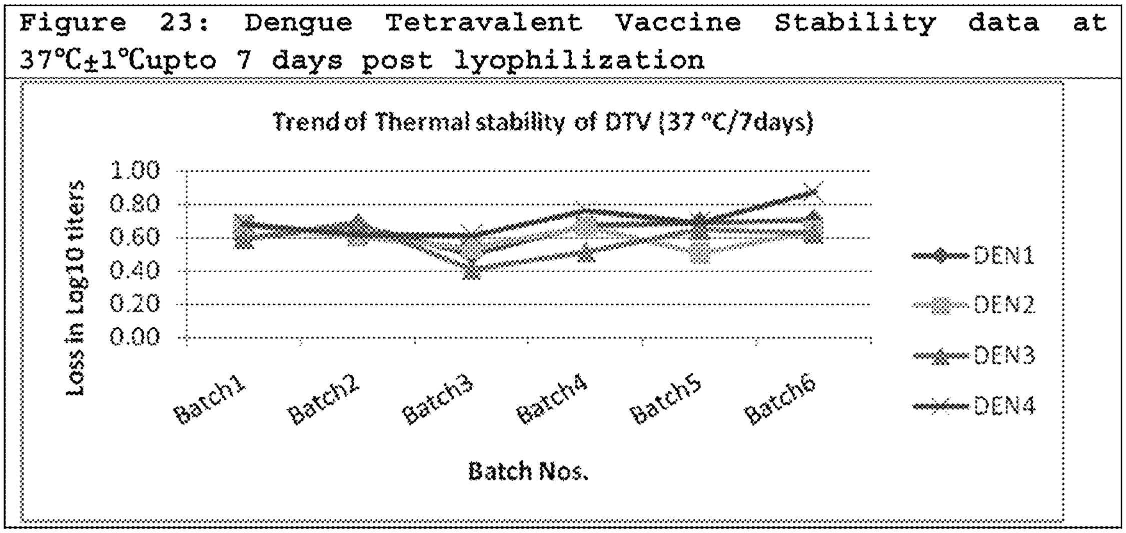
Figure 24: Dengue Tetravalent Vaccine Stability data at 42°C±1°Cupto 7 days post lyophilization
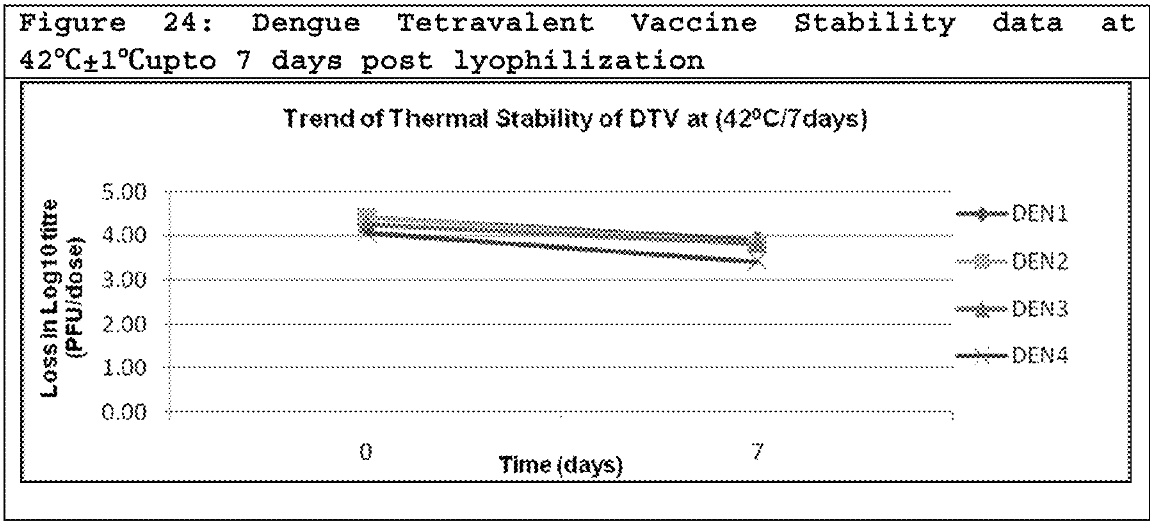

STABLE VACCINE COMPOSITIONS COMPRISING INTER ALIA LIVE ATTENUATED RECOMBINANT FLAVIVIRUS AND PROCESS FOR PREPARATION THEREOF

CROSS-REFERENCE TO RELATED APPLICATIONS

This application is a National Stage of International patent application PCT/IN2018/050645, filed on Oct. 10, 2018, which claims priority to foreign Indian patent application No. IN 201721036696, filed on Oct. 16, 2017, the disclosures of which are incorporated by reference in their entirety.

FIELD OF INVENTION

The present disclosure relates to the field of biotechnology, more particularly, it relates to a live attenuated flavivirus vaccine composition and the method of preparing the same. The present disclosure further relates to an improved methodology in the field of live attenuated flavivirus vaccine production.

BACKGROUND

The flavivirus genome consists of single stranded, positive sense, RNA molecule of 11 kilobases, containing single open reading frame. The RNA is translated into a polyprotein that is processed into at least 10 gene products: 3 structural proteins—Nucleocapsid or Core (C), Premembrane (prM), & Envelope (E) & 7 non-structural (NS) proteins—NS1, 2A, 2B, 3, 4A, 4B, & 5. (Lindenbach B D, et al., In: Fields Virology. Edited by Knipe D M, Howley P M, Griffin P E, et al. Philadelphia: Wolters Kluwer, Lippencott Williams and Wilkins; 2007. pp. 1101-1152). A number of these flaviviruses use arthropods (e.g., biting ticks and/or mosquitoes) as a means for transmission to virus recipients. Such arthropod-borne viruses (i.e., arboviruses) constitute a major worldwide health concern due to their highly pathogenic nature in humans. (Fernandez-Garcia M D, et al., Cell Host Microbe, 2009, 5:318-328). More specifically, human arbovirus pathogens include yellow fever (YF), Japanese encephalitis (JE), dengue (DEN), West Nile (WN) and tick-borne encephalitis (TBE) viruses that exist in nature in life cycles which involve mosquito or tick vectors and avian and/or mammalian competent reservoir hosts. (Gubler D, et al., In: Fields Virology. Edited by Knipe D M, Howley P M, Griffin P E, et al. 5th ed. Philadelphia: Wolters Kluwer, Lippencott Williams and Wilkins; 2007. pp. 1153-1252).

Yet, Dengue virus (DENV) have become the most important human arbovirus worldwide with estimates of as many as 500 million dengue infections occurring annually, resulting in more than 2 million cases of severe disease known as dengue hemorrhagic fever/dengue shock syndrome and 21000 deaths. There are four serotypes of dengue virus DENV1 DENV2, DENV3, and DENV4).

Numerous methods are known for producing live attenuated recombinant flavivirus preparations for vaccine and other purposes. Compositions and methods useful in freezing, lyophilizing, or otherwise storing viable virus preparations for laboratory or vaccine use in order to preserve their activity are also known.

The aqueous compositions of flaviviruses do not allow good viral stability in the long term and at a temperature above 5° C. By way of example, the bulk aqueous compositions of the YF-DEN (yellow fever-dengue) chimera lose more than 4 log, stabilized in liquid after storage for 1 day at 37° C. Now, the thermostability represents a serious problem in subtropical Dengue-endemic countries where transport under cold-chain conditions is difficult.

Lyophilization is a common mode of stabilization of vaccines. However, lyophilization causes loss in virus potency. Vaccines lose potency over time and the rate of potency loss is temperature-dependent. Live viruses are susceptible to osmotic, thermal and vacuum shocks. Enveloped viruses possess a lipid bilayer, which is considered as the less stable virus component because of its high fragility.

Live viruses are susceptible to various stresses during lyophilization steps like freezing, primary drying, secondary drying that could affect the physico-chemical stability of viruses. Owing to their structure, loss of potency during freeze-drying can be due to protein destabilization (e.g. unfolding, degradation, and aggregation), nucleic acid degradation, lipid layer alteration (e.g. phase transition, mechanical damage) and stresses related to changes in the internal (ice formation) and external (pH and osmolarity change) virus environment. The dehydration step of lyophilization results in collapse of the hydrogen bond structure of proteins which is accompanied with increased mobility of amino acid components of virus epitopes. It has been reported that in some cases lyophilization causes up to 40% loss in virus potency.

Though a lot of information is available on stress mechanisms and stabilization strategies of pharmaceutical peptides, proteins and DNA during lyophilization, due to the molecular complexity of viruses, different destabilization pathways and lack of analytical techniques permitting measurement of physico-chemical changes in the antigen's structure during and after lyophilization mean that viruses constitute a particular lyophilization challenge. The destabilization mechanisms as well as protection mechanisms for live, attenuated viral vaccines during lyophilization are not well known.

Hansen et al 2015 (Freeze-drying of live virus vaccines: A review, Hansen et al., Vaccine 33 (2015) 5507-5519) discloses a compilation of several freeze dried virus vaccine formulation (s) wherein majority of the formulations mention about preferential use of sugar alcohol/protein additive (i.e. Sucrose+Trehalose, Sorbitol, Hydrolyzed gelatin, Lactalbumin hydrolysates) for obtaining a lyophilized virus vaccine.

Following flavivirus vaccine formulations have been previously reported—1) Sorbitol, Trehalose, Urea, 2) Lactose, Sorbitol, HSA, 3) Lactose, Mannitol, HSA; 4) Poloxamer, Human Albumin, Trehalose, PBS; 5) Trehalose, Recombinant HSA, F127 (polyoxyethylene polyoxypropylene block copolymer).

In the case of HSA, the inclusion of these materials may raise potential safety concerns if these materials are derived from at-risk human or animal sources. Such added proteins are of concern for two main reasons. The first concern arises from the potential for animal- and human-derived protein to contain one or more adventitious agents. The second concern arises from the potential for animal- or human-derived protein to elicit an allergic reaction in susceptible individuals. Also, previously reported lyophilized vaccine formulation uses proteins which, even if produced using processes supporting high yields, have a cost implications for formulations. "For a vaccine to be broadly adopted in low income regions it is crucial to keep the cost of vaccine and its components such as stabilizers low. It is also crucial from the regulatory and safety point of view that excipients and stabilizers used should contain neither substances of animal origin nor contain animal component. Animal-derived compounds represent a potential danger due to the possible contamination with the scarpie-prion-protein (PrPSC) and the new variant of the Creutzefeld-Jakob disease (vCJD).

Nonionic surfactants used in pharmaceutical formulations include Triton™ X-100, Pluronic® F-68, F-88, and F-127 (poloxamers), Brij 35 (polyoxy-ethylene alkyl ether), polyoxyl stearate 40, Cremophor® EL, and alpha-tocopherol TPGS. Each of these surfactants have in common the fact that they all contain polyoxyethylene moieties and thus to a greater or lesser extent, exhibit a similar problem, in that the polyoxyethylene moiety auto oxidizes to produce reactive peroxides, which causes an increase in unwanted protein immunogenicity. (Refer Edward T. Maggio et al; Polysorbates, peroxides, protein aggregation, immunogenicity—a growing concern; Journal of Excipients and Food Chemicals 3(2):46-53; 2012).

PVP has been reported to destabilize live attenuated virus formulations. (Refer: JA White et al; Development of a stable liquid formulation of live attenuated influenza vaccine; Vaccine Volume 34, Issue 32, 12 Jul. 2016, Pages 3676-3683; 2016).

Trehalose is costly; it has to be combined with other sugars and protein additives (Gelatin) to achieve stability. Also, other stabilizers are better than trehalose for enhancing shelf life stability of a lyophilized vaccine.

Sorbitol has a low glass-transition temperature (Tg)(−1.6 Deg C.), therefore cannot be used as a main formulation component. The low Tg of sorbitol limits its use. Sorbitol has to be combined with other sugars and protein additives (Gelatin) to achieve stability.

Typically, recombinant viruses have been stored as freeze-dried pellets containing hydrolysates of casein and/or collagen in phosphate-buffered physiological saline (PBS). These pellets are then re-hydrated in a pharmaceutically acceptable solution such as 0.4-0.9% NaCl. However, there are significant disadvantages associated with such formulations and are known in the art. Among these are incompletely defined components, complex preparation procedures, high cost, and inability to maintain certain desired characteristics of the virus.

Flavivirus vaccine formulations developed previously has been stable at 2-8 deg C. for; 6 months, 25 deg C. for 7 days and at 37 deg C. for 1-2 days. There remains a need for developing formulations that comprise of minimum number of excipients and impart long term thermostability to flavivirus vaccines, in particular the live attenuated recombinant/chimeric Dengue viruses.

Such compositions/formulations and process for preparing of the same are described herein.

SUMMARY

The present disclosure provides an immunogenic composition comprising at least one live attenuated flavivirus, atleast one carbohydrate, and atleast one amino acid wherein, the composition is amenable to rapid freeze-drying treatments and the reconstituted composition preserves the desired characteristics of a virus, including virus viability, immunogenicity and stability.

The present disclosure more particularly relates to a lyophilized immunogenic compositions comprising:

a) Live attenuated recombinant/chimeric dengue virus, wherein the live attenuated dengue virus strains used are rDEN1Δ30-1545; rDEN2/4Δ30(ME)-1495, 7163; rDEN3Δ30/31-7164 and rDEN4Δ30-7132, 7163, 8308 obtained from the United States National Institutes of Health (NIH).
b) Sucrose about 3% w/v to about 6% w/v
c) Glycine about 3% w/v to about 6% w/v The present disclosure further provides a method for manufacturing such vaccine composition/formulation.

OBJECTS

Some of the objects of the present disclosure, which at least one embodiment herein satisfies, are as follows:

An object of the present disclosure is to ameliorate one or more problems of the prior art or to at least provide a useful alternative.

Another object of the present disclosure is to provide a stabilizing lyophilized vaccine compositions/formulations comprising of atleast one flavivirus, atleast one carbohydrate, atleast one amino acid, and optionally base. Wherein, the composition preserves desired characteristics of a virus, including virus viability, immunogenicity and stability.

Yet another object of the present disclosure is to provide a stabilizing lyophilized vaccine compositions/formulations comprising inter alia a live attenuated recombinant/chimeric dengue virus serotypes (DEN 1, DEN 2, DEN 3, DEN 4) suitable for treating or preventing dengue infection, or to prevent, ameliorate, or delay the onset or progression of the clinical manifestations thereof.

Yet another object of the present disclosure is to provide a method for manufacturing such vaccine composition/formulation.

Other objects and advantages of the present disclosure will be more apparent from the following description, which is not intended to limit the scope of the present disclosure.

DETAILED DESCRIPTION

Although the present disclosure may be susceptible to different embodiments, certain embodiments are shown in the figures and following detailed discussion, with the understanding that the present disclosure can be considered an exemplification of the principles of the disclosure and is not intended to limit the scope of disclosure to that which is illustrated and disclosed in this description.

According to a first embodiment of the present disclosure, an immunogenic composition comprising one or more live attenuated flaviviruses, one or more carbohydrate, and one or more amino acid wherein, the composition is amenable to rapid freeze-drying treatments and the reconstituted composition preserves the desired characteristics of a virus, including virus viability, immunogenicity and stability.

The term "live" is used in its conventional meaning, a live virus is a virus which has not been inactivated, i.e. a virus capable of replicating on permissive cells. A live attenuated flavivirus is a virus which does not induce the disease caused by the corresponding wild-type virus in animals or humans and which is capable of inducing a specific immune response.

According to a second embodiment of the present disclosure, the one or more live attenuated flaviviruses are a recombinant flaviviruses and/or a chimeric flaviviruses.

According to a third embodiment of the present disclosure, one or more live attenuated flaviviruses is selected from the group consisting of dengue (DEN) virus, yellow fever (YF) virus, Japanese encephalitis (JE) virus, Kunjin virus, West Nile (WN) virus, tick-borne encephalitis (TBE)

virus, St. Louis encephalitis virus, Murray Valley encephalitis virus, Zika virus, or any related flavivirus thereof.

Yet according to the preferred aspect of the third embodiment, one or more live attenuated flaviviruses is dengue (DEN) virus, optionally a plurality of live attenuated dengue (DEN) viruses of different serotypes selected from group of DEN-1, DEN-2, DEN-3 and DEN-4.

According to a fourth embodiment of the present disclosure, one or more live attenuated flaviviruses is selected from the group consisting of live attenuated chimeric/recombinant yellow fever (YF) viruses and/or of a live attenuated chimeric/recombinant Japanese encephalitis (JE) viruses, and/or of a live attenuated chimeric/recombinant dengue (DEN) viruses, and/or of a live attenuated chimeric/recombinant West Nile (WN) viruses and/or of a live attenuated chimeric/recombinant tick-borne encephalitis (TBE) viruses and/or of a chimeric dengue virus (yellow fever-dengue) virus, and/or of a chimeric YF-WN (yellow fever-West Nile virus) virus and/or of a chimeric YF-JE (yellow fever-Japanese encephalitis) virus or any related flavivirus thereof.

Yet according to a preferred aspect of fourth embodiment, one or more live attenuated flaviviruses is live attenuated chimeric/recombinant dengue (DEN) viruses.

According to a fifth embodiment of the present disclosure, live attenuated recombinant/chimeric dengue viruses used in immunogenic composition is described below:

A) Brief Description of NIH Recombinant Strains/its Construction:

All the activities related to generation of attenuated vaccine strains of all the four dengue virus serotypes (DEN 1, DEN 2, DEN 3, & DEN 4) explained below have been conducted at NIH, US. Contents of WO2002095075 and WO2008022196 are incorporated herein in entirety.

Origin of the Gene

1. Each of the attenuated strain of dengue virus serotype 1-4 (rDEN1Δ30, rDEN2/4Δ30(ME), rDEN3Δ30/31 & rDEN4Δ30) has been developed by deletion of around 30 nucleotides (Δ30) (additional 31 nucleotide (Δ31) in case of DEN-3) from the non-translational 3' end of the wild type strains. The Δ31 mutation can also be generated alone to discern the contribution of either Δ30 or Δ31 in the combined Δ30/31 deletion mutation.
2. The DEN 2 virus serotype has been developed by replacing the M and E protein of the attenuated DEN 4 serotype with that of DEN 2 M and E protein.
3. Structurally all the four strains are enveloped positive sense RNA viruses of 35-50 nanometer size.
4. The rDEN1Δ30-1545 strain used herein encodes a single Lys→Arg mutation at amino acid residue number 484 (A1545G mutation) in the viral polyprotein.
5. The rDEN2/4Δ30(ME)-1495, 7163 strain used herein encodes a Ser→Phe mutation at amino acid residue number 186 (C1495T mutation) and a Leu→Phe mutation at amino acid residue number 112 (A7163C mutation) in the viral polyprotein.
6. rDEN3Δ30/31 includes the original Δ30 deletion and a non-contiguous 31 nucleotide deletion that removes both the original TL-2 and TL-3 structures. The resultant rDEN3Δ30/31-7164 strain used herein encodes a Val→Ala mutation at amino acid residue number 115 (T7164C mutation) in the viral polyprotein.
7. The rDEN4Δ30-7132, 7163, 8308 strain used herein encodes a Thr→Ile mutation at amino acid residue number 102 (C7132T mutation), a Leu→Phe mutation at amino acid residue number 112 (A7163C mutation) and a Lys→Arg mutation at amino acid residue number 249 (A8308G mutation) in the viral polyprotein.

Figures Depicting the RNA Sequence and the Virus Structure of the DEN Vaccine Strains:

Refer FIGS. 1, 2 and 3

The wild type strains used for the generation of vaccine strains are given in Table below:

TABLE 1

Nomenclature of wild type and vaccine strains

| Serotype | Wild type strain | Vaccine strain |
|---|---|---|
| DEN 1 | Western Pacific strain | rDEN1Δ30-1545 |
| DEN 2 | New Guinea strain | rDEN2/4Δ30(ME)-1495, 7163 |
| DEN 3 | Sleman/78 | rDEN3Δ30/31-7164 |
| DEN 4 | Dominica | rDEN4Δ30-7132, 7163, 8308 |

B) Transformation Procedure:

For the generation of dengue virus vaccine strains essentially the following steps were followed—

1. Plasmid containing full length cDNA copy of the wild type DEN virus was created by generation of short DNA segments using reverse transcriptase and PCR. Fragments so obtained were appropriately ligated to generate an intact double stranded DNA comprising of the full length genomic cDNA strand of the wild type DEN that was cloned in a plasmid.
2. Δ30 mutation was inserted by mutating a sub fragment of the 3'UTR and replacing the 3'UTR of the wild type DEN with the sub fragment containing the Δ30 region. Specific mutations were introduced by site specific PCR mutagenesis.
3. For the generation of DEN 2 vaccine strain structural genes M and E, of DEN 2 were cloned in plasmid and used to replace the structural genes in the DEN 4 cloned plasmid containing the Δ30 mutation. For the generation of DEN 3 vaccine strain two deletions of 30 and 31 nucleotides was introduced in the wild type clone.
4. Genome length capped RNA transcripts were synthesized from linearized plasmids using AmpliCap SP6 Message Maker Kit (EpiCentre Technologies, Madison) and the RNA purified using the RNeasy Mini kit (Qiagen, Valencia, Calif.). Vero cells (C6/36 for dengue 3) were transfected with purified RNA transcripts using DOTAP liposomal transfection reagents (Roche, Indianapolis, Ind.) to recover desired virus. Rescued viruses were subjected to amplification, terminal dilution cloning and final amplification for the generation of seed virus in Vero cells. Details on number of cycles of amplification and terminal dilution undertaken for each strain are tabulated below in table 2.

TABLE 2

Cycle of amplification and terminal dilution for seed virus preparation

| Virus strain | DEN 1 | DEN 2 | DEN 3 | DEN 4 |
|---|---|---|---|---|
| Rescued in | Vero | Vero | C6/36* | Vero |
| Amplification | Nil | Nil | 6× | 3× |
| Terminal dilution cloning | 2× | 2× | 3× | 3× |
| Amplification | 2× | 2× | 2× | 2× |

*All further work of amplification and terminal dilution cloning was carried out in Vero cells.

According to a first aspect of the fifth embodiment, the chimeric viruses have the particularity of exhibiting the characteristics of the live attenuated viruses as defined above. It is therefore possible to use, in the context of the disclosure, any chimeric virus expressing the envelope protein or one or more epitopes of one or more envelope protein(s) of one or more flaviviruses and inducing a specific immune response comprising antibodies which neutralize the strain, or at least one of the strains, from which the envelope protein or said epitope is derived.

According to a second aspect of the fifth embodiment, the live attenuated recombinant dengue virus nucleic acid further comprises a mutation generating a mutant having a phenotype selected from the group consisting of temperature sensitivity in Vero cells or the human liver cell line HuH-7, host-cell restriction in mosquito cells or the human liver cell line HuH-7, host-cell adaptation for improved replication in Vero cells, or attenuation in mice or monkeys, wherein the composition comprising a member selected from the group consisting of:

(1) rDENIΔ30, rDEN2Δ30, rDEN3Δ30, rDEN4Δ30,
(2) rDENIΔ30, rDEN2Δ30, rDEN3Δ30, rDEN4/IΔ30,
(3) rDENIΔ30, rDEN2Δ30, rDEN3Δ30, rDEN4/2Δ30,
(4) rDENIΔ30, rDEN2Δ30, rDEN3Δ30, rDEN4/3Δ30,
(5) rDENIΔ30, rDEN2Δ30, rDEN3/IΔ30, rDEN4Δ30,
(6) rDENIΔ30, rDEN2Δ30, rDEN3/IΔ30, rDEN4/IΔ30,
(7) rDENIΔ30, rDEN2Δ30, rDEN3/IΔ30, rDEN4/2Δ30,
(8) rDENIΔ30, rDEN2Δ30, rDEN3/IΔ30, rDEN4/3Δ30,
(9) rDENIΔ30, rDEN2Δ30, rDEN3/2Δ30, rDEN4Δ30,
(10) rDENIΔ30, rDEN2Δ30, rDEN3/2Δ30, rDEN4/IΔ30,
(11) rDENIΔ30, rDEN2Δ30, rDEN3/2Δ30, rDEN4/2Δ30,
(12) rDENIΔ30, rDEN2Δ30, rDEN3/2Δ30, rDEN4/3Δ30,
(13) rDENIΔ30, rDEN2Δ30, rDEN3/4Δ30, rDEN4Δ30,
(14) rDENIΔ30, rDEN2Δ30, rDEN3/4Δ30, rDEN4/IΔ30,
(15) rDEMΔ30, rDEN2Δ30, rDEN3/4Δ30, rDEN4/2Δ30,
(16) rDENIΔ30, rDEN2Δ30, rDEN3/4Δ30, rDEN4/3Δ30,
(17) rDENIΔ30, rDEN2/IΔ30, rDEN3Δ30, rDEN4Δ30,
(18) rDENIΔ30, rDEN2/IΔ30, rDEN3Δ30, rDEN4/IΔ30,
(19) rDENIΔ30, rDEN2/IΔ30, rDEN3Δ30, rDEN4/2Δ30,
(20) rDENIΔ30, rDEN2/IΔ30, rDEN3Δ30, rDEN4/3Δ30,
(21) rDENIΔ30, rDEN2/IΔ30, rDEN3/IΔ30, rDEN4Δ30,
(22) rDENIΔ30, rDEN2/IΔ30, rDEN3/IΔ30, rDEN4/IΔ30,
(23) rDENIΔ30, rDEN2/IΔ30, rDEN3/IΔ30, rDEN4/2Δ30,
(24) rDENIΔ30, rDEN2/IΔ30, rDEN3/IΔ30, rDEN4/3Δ30,
(25) rDENIΔ30, rDEN2/IΔ30, rDEN3/2Δ30, rDEN4Δ30,
(26) rDENIΔ30, rDEN2/IΔ30, rDEN3/2Δ30, rDEN4/IΔ30,
(27) rDEMΔ30, rDEN2/IΔ30, rDEN3/2Δ30, rDEN4/2Δ30,
(28) rDENIΔ30, rDEN2/IΔ30, rDEN3/2Δ30, rDEN4/3Δ30,
(29) rDENIΔ30, rDEN2/IΔ30, rDEN3/4Δ30, rDEN4Δ30,
(30) rDENIΔ30, rDEN2/IΔ30, rDEN3/4Δ30, rDEN4/IΔ30,
(31) rDENIΔ30, rDEN2/IΔ30, rDEN3/4Δ30, rDEN4/2Δ30,
(32) rDENIΔ30, rDEN2/IΔ30, rDEN3/4Δ30, rDEN4/3Δ30,
(33) rDENIΔ30, rDEN2/3Δ30, rDEN3Δ30, rDEN4Δ30,
(34) rDENIΔ30, rDEN2/3Δ30, rDEN3Δ30, rDEN4/IΔ30,
(35) rDENIΔ30, rDEN2/3Δ30, rDEN3Δ30, rDEN4/2Δ30,
(36) rDENIΔ30, rDEN2/3Δ30, rDEN3Δ30, rDEN4/3Δ30,
(37) rDENIΔ30, rDEN2/3Δ30, rDEN3/IΔ30, rDEN4Δ30,
(38) rDENIΔ30, rDEN2/3Δ30, rDEN3/IΔ30, rDEN4/IΔ30,
(39) rDENIΔ30, rDEN2/3Δ30, rDEN3/IΔ30, rDEN4/2Δ30,
(40) rDENIΔ30, rDEN2/3Δ30, rDEN3/IΔ30, rDEN4/3Δ30,
(41) rDENIΔ30, rDEN2/3Δ30, rDEN3/2Δ30, rDEN4Δ30,
(42) rDENIΔ30, rDEN2/3Δ30, rDEN3/2Δ30, rDEN4/IΔ30,
(43) rDENIΔ30, rDEN2/3Δ30, rDEN3/2Δ30, rDEN4/2Δ30,
(44) rDENIΔ30, rDEN2/3Δ30, rDEN3/2Δ30, rDEN4/3Δ30,
(45) rDENIΔ30, rDEN2/3Δ30, rDEN3/4Δ30, rDEN4Δ30,
(46) rDENIΔ30, rDEN2/3Δ30, rDEN3/4Δ30, rDEN4/IΔ30,
(47) rDENIΔ30, rDEN2/3Δ30, rDEN3/4Δ30, rDEN4/2Δ30,
(48) rDENIΔ30, rDEN2/3Δ30, rDEN3/4Δ30, rDEN4/3Δ30,
(49) rDENIΔ30, rDEN2/4Δ30, rDEN3Δ30, rDEN4Δ30,
(50) rDENIΔ30, rDEN2/4Δ30, rDEN3Δ30, rDEN4/IΔ30,
(51) rDENIΔ30, rDEN2/4Δ30, rDEN3Δ30, rDEN4/2Δ30,
(52) rDENIΔ30, rDEN2/4Δ30, rDEN3Δ30, rDEN4/3Δ30,
(53) rDENIΔ30, rDEN2/4Δ30, rDEN3/IΔ30, rDEN4Δ30,
(54) rDENIΔ30, rDEN2/4Δ30, rDEN3/IΔ30, rDEN4/IΔ30,
(55) rDENIΔ30, rDEN2/4Δ30, rDEN3/IΔ30, rDEN4/2Δ30,
(56) rDENIΔ30, rDEN2/4Δ30, rDEN3/IΔ30, rDEN4/3Δ30,
(57) rDENIΔ30, rDEN2/4Δ30, rDEN3/2Δ30, rDEN4Δ30,
(58) rDENIΔ30, rDEN2/4Δ30, rDEN3/2Δ30, rDEN4/IΔ30,
(59) rDENIΔ30, rDEN2/4Δ30, rDEN3/2Δ30, rDEN4/2Δ30,
(60) rDENIΔ30, rDEN2/4Δ30, rDEN3/2Δ30, rDEN4/3Δ30,
(61) rDENIΔ30, rDEN2/4Δ30, rDEN3/4Δ30, rDEN4Δ30,
(62) rDENIΔ30, rDEN2/4Δ30, rDEN3/4Δ30, rDEN4/IΔ30,
(63) rDENIΔ30, rDEN2/4Δ30, rDEN3/4Δ30, rDEN4/2Δ30,
(64) rDENIΔ30, rDEN2/4Δ30, rDEN3/4Δ30, rDEN4/3Δ30,
(65) rDENI/2Δ30, rDEN2Δ30, rDEN3Δ30, rDEN4Δ30,
(66) rDENI/2Δ30, rDEN2Δ30, rDEN3Δ30, rDEN4/IΔ30,
(67) rDENI/2Δ30, rDEN2Δ30, rDEN3Δ30, rDEN4/2Δ30,
(68) rDENI/2Δ30, rDEN2Δ30, rDEN3Δ30, rDEN4/3Δ30,
(69) rDENI/2Δ30, rDEN2Δ30, rDEN3/IΔ30, rDEN4Δ30,
(70) rDENI/2Δ30, rDEN2Δ30, rDEN3/IΔ30, rDEN4/IΔ30,
(71) rDENI/2Δ30, rDEN2Δ30, rDEN3/IΔ30, rDEN4/2Δ30,
(72) rDENI/2Δ30, rDEN2Δ30, rDEN3/IΔ30, rDEN4/3Δ30,
(73) rDENI/2Δ30, rDEN2Δ30, rDEN3/2Δ30, rDEN4Δ30,
(74) rDENI/2Δ30, rDEN2Δ30, rDEN3/2Δ30, rDEN4/IΔ30,
(75) rDENI/2Δ30, rDEN2Δ30, rDEN3/2Δ30, rDEN4/2Δ30,
(76) rDENI/2Δ30, rDEN2Δ30, rDEN3/2Δ30, rDEN4/3Δ30,
(77) rDENI/2Δ30, rDEN2Δ30, rDEN3/4Δ30, rDEN4Δ30,
(78) rDENI/2Δ30, rDEN2Δ30, rDEN3/4Δ30, rDEN4/IΔ30,
(79) rDENI/2Δ30, rDEN2Δ30, rDEN3/4Δ30, rDEN4/2Δ30, i

(80) rDENI/2Δ30, rDEN2Δ30, rDEN3/4Δ30, rDEN4/3Δ30,

(81) rDENI/2Δ30, rDEN2/IΔ30, rDEN3Δ30, rDEN4Δ30,

(82) rDENI/2Δ30, rDEN2/IΔ30, rDEN3Δ30, rDEN4/IΔ30,

(83) rDENI/2Δ30, rDEN2/IΔ30, rDEN3Δ30, rDEN4/2Δ30,

(84) rDENI/2Δ30, rDEN2/IΔ30, rDEN3Δ30, rDEN4/3Δ30,

(85) rDENI/2Δ30, rDEN2/IΔ30, rDEN3/IΔ30, rDEN4Δ30,

(86) rDENI/2Δ30, rDEN2/IΔ30, rDEN3/IΔ30, rDEN4/IΔ30,

(87) rDENI/2Δ30, rDEN2/IΔ30, rDEN3/IΔ30, rDEN4/2Δ30,

(88) rDENI/2Δ30, rDEN2/IΔ30, rDEN3/IΔ30, rDEN4/3Δ30,

(89) rDENI/2Δ30, rDEN2/IΔ30, rDEN3/2Δ30, rDEN4Δ30, i

(90) rDENI/2Δ30, rDEN2/IΔ30, rDEN3/2Δ30, rDEN4/IΔ30,

(91) rDENI/2Δ30, rDEN2/IΔ30, rDEN3/2Δ30, rDEN4/2Δ30,

(92) rDENI/2Δ30, rDEN2/IΔ30, rDEN3/2Δ305 rDEN4/3Δ30,

(93) rDENI/2Δ30, rDEN2/IΔ30, rDEN3/4Δ30, rDEN4Δ30,

(94) rDENI/2Δ30, rDEN2/IΔ30, rDEN3/4Δ30, rDEN4/IΔ30,

(95) rDENI/2Δ30, rDEN2/IΔ30, rDEN3/4Δ30, rDEN4/2Δ30,

(96) rDENI/2Δ30, rDEN2/IΔ30, rDEN3/4Δ30, rDEN4/3Δ30,

(97) rDENI/2Δ30, rDEN2/3Δ30, rDEN3Δ30, rDEN4Δ30,

(98) rDENI/2Δ30, rDEN2/3Δ30, rDEN3Δ30, rDEN4/IΔ30,

(99) rDENI/2Δ30, rDEN2/3Δ30, rDEN3Δ30, rDEN4/2Δ30, i (100) rDENI/2Δ30, rDEN2/3Δ30, rDEN3Δ30, rDEN4/3Δ30, (101) rDENI/2Δ30, rDEN2/3Δ30, rDEN3/IΔ30, rDEN4Δ30, (102) rDENI/2Δ30, rDEN2/3Δ30, rDEN3/IΔ30, rDEN4/IΔ30, (103) rDENI/2Δ30, rDEN2/3Δ30, rDEN3/IΔ30, rDEN4/2Δ30, (104) rDENI/2Δ30, rDEN2/3Δ30, rDEN3/IΔ30, rDEN4/3Δ30, (105) rDENI/2Δ30, rDEN2/3Δ30, rDEN3/2Δ30, rDEN4Δ30, (106) rDENI/2Δ30, rDEN2/3Δ30, rDEN3/2Δ30, rDEN4/IΔ30, (107) rDENI/2Δ30, rDEN2/3Δ30, rDEN3/2Δ30, rDEN4/2Δ30, (108) rDENI/2Δ30, rDEN2/3Δ30, rDEN3/2Δ30, rDEN4/3Δ30, (109) rDENI/2Δ30, rDEN2/3Δ30, rDEN3/4Δ30, rDEN4Δ30, (110) rDENI/2Δ30, rDEN2/3Δ30, rDEN3/4Δ30, rDEN4/IΔ30, (111) rDENI/2Δ30, rDEN2/3Δ30, rDEN3/4Δ30, rDEN4/2Δ30, (112) rDENI/2Δ30, rDEN2/3Δ30, rDEN3/4Δ30, rDEN4/3Δ30, (113) rDENI/2Δ30, rDEN2/4Δ30, rDEN3Δ30, rDEN4Δ30, (114) rDENI/2Δ30, rDEN2/4Δ30, rDEN3Δ30, rDEN4/IΔ30, (115) rDENI/2Δ30, rDEN2/4Δ30, rDEN3Δ30, rDEN4/2Δ30, (116) rDENI/2Δ30, rDEN2/4Δ30, rDEN3Δ30, rDEN4/3Δ30, (117) rDENI/2Δ30, rDEN2/4Δ30, rDEN3/IΔ30, rDEN4Δ30, (118) rDENI/2Δ30, rDEN2/4Δ30, rDEN3/IΔ30, rDEN4/IΔ30, (119) rDENI/2Δ30, rDEN2/4Δ30, rDEN3/IΔ30, rDEN4/2Δ30, (120) rDENI/2Δ30, rDEN2/4Δ30, rDEN3/IΔ30, rDEN4/3Δ30, (121) rDENI/2Δ30, rDEN2/4Δ30, rDEN3/2Δ305 rDEN4Δ30, (122) rDENI/2Δ30, rDEN2/4Δ30, rDEN3/2Δ30, rDEN4/IΔ30, (123) rDENI/2Δ30, rDEN2/4Δ30, rDEN3/2Δ30, rDEN4/2Δ30, (124) rDENI/2Δ30, rDEN2/4Δ30, rDEN3/2Δ30, rDEN4/3Δ30, (125) rDENI/2Δ30, rDEN2/4Δ30, rDEN3/4Δ30, rDEN4Δ30, (126) rDENI/2Δ30, rDEN2/4Δ30, rDEN3/4Δ30, rDEN4/IΔ30, (127) rDENI/2Δ30, rDEN2/4Δ30, rDEN3/4Δ30, rDEN4/2Δ30, (128) rDENI/2Δ30, rDEN2/4Δ30, rDEN3/4Δ30, rDEN4/3Δ30, (129) rDENI/3Δ30, rDEN2Δ30, rDEN3Δ30, rDEN4Δ30, (130) rDENI/3Δ30, rDEN2Δ30, rDEN3Δ30, rDEN4/IΔ30, (131) rDENI/3Δ30, rDEN2Δ30, rDEN3Δ30, rDEN4/2Δ30, (132) rDENI/3Δ30, rDEN2Δ30, rDEN3Δ30, rDEN4/3Δ30, (133) rDENI/3Δ30, rDEN2Δ30, rDEN3/IΔ30, rDEN4Δ30, (134) rDENI/3Δ30, rDEN2Δ30, rDEN3/IΔ30, rDEN4/IΔ30, (135) rDENI/3Δ30, rDEN2Δ30, rDEN3/IΔ30, rDEN4/2Δ30, (136) rDENI/3Δ30, rDEN2Δ30, rDEN3/IΔ30, rDEN4/3Δ30, (137) rDENI/3Δ30, rDEN2Δ30, rDEN3/2Δ30, rDEN4Δ30, (138) rDENI/3Δ30, rDEN2Δ30, rDEN3/2Δ30, rDEN4/IΔ30, (139) rDENI/3Δ30, rDEN2Δ30, rDEN3/2Δ30, rDEN4/2Δ30, (140) rDENI/3Δ30, rDEN2Δ30, rDEN3/2Δ30, rDEN4/3Δ30, (141) rDENI/3Δ30, rDEN2Δ30, rDEN3/4Δ30, rDEN4Δ30, (142) rDENI/3Δ30, rDEN2Δ30, rDEN3/4Δ30, rDEN4/IΔ30, (143) rDENI/3Δ30, rDEN2Δ30, rDEN3/4Δ30, rDEN4/2Δ30, (144) rDENI/3Δ30, rDEN2Δ30, rDEN3/4Δ30, rDEN4/3Δ30, (145) rDENI/3Δ30, rDEN2/IΔ30, rDEN3Δ30, rDEN4Δ30, (146) rDENI/3Δ30, rDEN2/IΔ30, rDEN3Δ30, rDEN4/IΔ30, (147) rDENI/3Δ30, rDEN2/IΔ30, rDEN3Δ30, rDEN4/2Δ30, (148) rDENI/3Δ30, rDEN2/IΔ30, rDEN3Δ30, rDEN4/3Δ30, (149) rDENI/3Δ30, rDEN2/IΔ30, rDEN3/IΔ30, rDEN4Δ30, (150) rDENI/3Δ30, rDEN2/IΔ30, rDEN3/IΔ30, rDEN4/IΔ30, (151) rDENI/3Δ30, rDEN2/IΔ30, rDEN3/IΔ30, rDEN4/2Δ30, (152) rDENI/3Δ30, rDEN2/IΔ30, rDEN3/IΔ30, rDEN4/3Δ30, (153) rDENI/3Δ30, rDEN2/IΔ30, rDEN3/2Δ30, rDEN4Δ30, (154) rDENI/3Δ30, rDEN2/IΔ30, rDEN3/2Δ30, rDEN4/IΔ30, (155) rDENI/3Δ30, rDEN2/IΔ30, rDEN3/2Δ30, rDEN4/2Δ30, (156) rDENI/3Δ30, rDEN2/IΔ30, rDEN3/2Δ30, rDEN4/3Δ30, (157) rDENI/3Δ30, rDEN2/IΔ30, rDEN3/4Δ30, rDEN4Δ30, (158) rDENI/3Δ30, rDEN2/IΔ30, rDEN3/4Δ30, rDEN4/IΔ30, (159) rDENI/3Δ30, rDEN2/IΔ30, rDEN3/4Δ30, rDEN4/2Δ30, (160) rDENI/3Δ30, rDEN2/IΔ30, rDEN3/4Δ30, rDEN4/3Δ30, (161) rDENI/3Δ30, rDEN2/3Δ30, rDEN3Δ30, rDEN4Δ30, (162) rDENI/3Δ30, rDEN2/3Δ30, rDEN3Δ30, rDEN4/IΔ30, (163) rDENI/3Δ30, rDEN2/3Δ30, rDEN3Δ30, rDEN4/2Δ30, (164) rDENI/3Δ30, rDEN2/3Δ30, rDEN3Δ30, rDEN4/3Δ30, (165) rDENI/3Δ30, rDEN2/3Δ30, rDEN3/IΔ30, rDEN4Δ30, (166) rDENI/3Δ30, rDEN2/3Δ30, rDEN3/IΔ30, rDEN4/IΔ30, (167) rDENI/3Δ30, rDEN2/3Δ30, rDEN3/IΔ30, rDEN4/2Δ30, (168) rDENI/3Δ30, rDEN2/3Δ30, rDEN3/IΔ30, rDEN4/3Δ30, (169) rDENI/3Δ30, rDEN2/3Δ30, rDEN3/2Δ30, rDEN4Δ30, (170) rDENI/3Δ30, rDEN2/3Δ30, rDEN3/2Δ30, rDEN4/IΔ30, (171) rDENI/3Δ30, rDEN2/3Δ30, rDEN3/2Δ30, rDEN4/2Δ30, (172) rDENI/3Δ30, rDEN2/3Δ30, rDEN3/2Δ30, rDEN4/3Δ30, (173) rDENI/3Δ30, rDEN2/3Δ30, rDEN3/4Δ30, rDEN4Δ30, (174) rDENI/3Δ30, rDEN2/3Δ30, rDEN3/4Δ30, rDEN4/IΔ30, (175) rDENI/3Δ30, rDEN2/3Δ30, rDEN3/4Δ30, rDEN4/2Δ30, (176) rDENI/3Δ30, rDEN2/3Δ30, rDEN3/4Δ30, rDEN4/3Δ30, (177) rDENI/3Δ30, rDEN2/4Δ30, rDEN3Δ30, rDEN4Δ30, (178) rDENI/3Δ30, rDEN2/4Δ30, rDEN3Δ30, rDEN4/IΔ30, (179) rDENI/3Δ30, rDEN2/4Δ30, rDEN3Δ30, rDEN4/2Δ30, (180) rDENI/3Δ30, rDEN2/4Δ30, rDEN3Δ30, rDEN4/3Δ30, (181) rDENI/3Δ30, rDEN2/4Δ30, rDEN3/IΔ30, rDEN4Δ30, (182) rDENI/3Δ30, rDEN2/4Δ30, rDEN3/IΔ30, rDEN4/IΔ30, (183) rDENI/3Δ30, rDEN2/4Δ30, rDEN3/IΔ30, rDEN4/2Δ30, (184) rDENI/3Δ30, rDEN2/4Δ30, rDEN3/IΔ30, rDEN4/3Δ30, (185) rDENI/3Δ30, rDEN2/4Δ30, rDEN3/2Δ30, rDEN4Δ30, (186) rDENI/3Δ30, rDEN2/4Δ30, rDEN3/2Δ30, rDEN4/IΔ30, (187) rDENI/3Δ30, rDEN2/4Δ30, rDEN3/2Δ30, rDEN4/2Δ30, (188) rDENI/3Δ30, rDEN2/4Δ30, rDEN3/2Δ30, rDEN4/3Δ30, (189) rDENI/3Δ30, rDEN2/4Δ30, rDEN3/4Δ30, rDEN4Δ30, (190) rDENI/3Δ30, rDEN2/4Δ30, rDEN3/4Δ30, rDEN4/IΔ30, (191) rDENI/3Δ30, rDEN2/4Δ30, rDEN3/4Δ30, rDEN4/2Δ30, (192) rDENI/3Δ30, rDEN2/4Δ30, rDEN3/4Δ30, rDEN4/3Δ30, (193) rDENI/4Δ30, rDEN2Δ30, rDEN3Δ30, rDEN4Δ30, (194) rDENI/4Δ30, rDEN2Δ30, rDEN3Δ30, rDEN4/IΔ30, (195) rDENI/4Δ30, rDEN2Δ30, rDEN3Δ30, rDEN4/2Δ30, (196) rDENI/4Δ30, rDEN2Δ30, rDEN3Δ30, rDEN4/3Δ30, (197) rDENI/4Δ30, rDEN2Δ30, rDEN3/IΔ30, rDEN4Δ30, (198) rDENI/4Δ30, rDEN2Δ30, rDEN3/IΔ30, rDEN4/IΔ30, (199) rDENI/4Δ30, rDEN2Δ30, rDEN3/IΔ30, rDEN4/2Δ30, (200) rDENI/4Δ30, rDEN2Δ30, rDEN3/IΔ30, rDEN4/3Δ30, (201) rDENI/4Δ30, rDEN2Δ30, rDEN3/2Δ30, rDEN4Δ30, (202) rDENI/4Δ30, rDEN2Δ30, rDEN3/2Δ30, rDEN4/IΔ30, (203) rDENI/4Δ30, rDEN2Δ30, rDEN3/2Δ30, rDEN4/2Δ30, (204) rDENI/4Δ30, rDEN2Δ30, rDEN3/2Δ30, rDEN4/3Δ30, (205) rDENI/4Δ30, rDEN2Δ30, rDEN3/4Δ30, rDEN4Δ30, (206) rDENI/4Δ30, rDEN2Δ30, rDEN3/4Δ30, rDEN4/IΔ30, (207) rDENI/4Δ30, rDEN2Δ30, rDEN3/4Δ30, rDEN4/2Δ30, (208) rDENI/4Δ30, rDEN2Δ30, rDEN3/4Δ30, rDEN4/3Δ30, (209) rDENI/4Δ30, rDEN2/IΔ30, rDEN3Δ30, rDEN4Δ30, (210) rDENI/4Δ30, rDEN2/IΔ30, rDEN3Δ30, rDEN4/IΔ30, (211) rDENI/4Δ30, rDEN2/IΔ30, rDEN3Δ30, rDEN4/2Δ30, (212) rDENI/4Δ30, rDEN2/IΔ30, rDEN3Δ30, rDEN4/3Δ30, (213) rDENI/4Δ30, rDEN2/IΔ30, rDEN3/IΔ30, rDEN4Δ30, (214) rDENI/4Δ30, rDEN2/IΔ30, rDEN3/1Δ30, rDEN4/IΔ30, (215) rDENI/4Δ30, rDEN2/IΔ30, rDEN3/IΔ30, rDEN4/2Δ30, (216) rDENI/4Δ30, rDEN2/IΔ30, rDEN3/IΔ30, rDEN4/3Δ30, (217) rDENI/4Δ30, rDEN2/IΔ30, rDEN3/2Δ30, rDEN4Δ30, (218) rDENI/4Δ30$_5$rDEN2/IΔ30, rDEN3/2Δ30, rDEN4/IΔ30, (219) rDENI/4Δ30, rDEN2/IΔ30, rDEN3/2Δ30, rDEN4/2Δ30, (220) rDENI/4Δ30, rDEN2/IΔ30, rDEN3/2Δ30, rDEN4/3Δ30, (221) rDENI/4Δ30, rDEN2/IΔ30, rDEN3/4Δ30, rDEN4Δ30, (222) rDENI/4Δ30, rDEN2/IΔ30, rDEN3/4Δ30, rDEN4/IΔ30, (223) rDENI/4Δ30, rDEN2/IΔ305 rDEN3/4Δ30, rDEN4/2Δ30, (224) rDENI/4Δ30, rDEN2/IΔ30, rDEN3/4Δ30, rDEN4/3Δ30, (225) rDENI/4Δ30, rDEN2/3Δ30, rDEN3Δ30, rDEN4Δ30, (226) rDENI/4Δ30, rDEN2/3Δ30, rDEN3Δ30, rDEN4/IΔ30, (227) rDENI/4Δ30, rDEN2/3Δ30, rDEN3Δ30, rDEN4/2Δ30, (228) rDENI/4Δ30, rDEN2/3Δ30, rDEN3Δ30, rDEN4/3Δ30, (229) rDENI/4Δ30, rDEN2/3Δ30, rDEN3/IΔ30, rDEN4Δ30, (230) rDENI/4Δ30, rDEN2/3Δ30, rDEN3/IΔ30, rDEN4/IΔ30, (231) rDENI/4Δ30, rDEN2/3Δ30, rDEN3/IΔ30, rDEN4/2Δ30, (232) rDENI/4Δ30, rDEN2/3Δ30, rDEN3/IΔ30, rDEN4/3Δ30, (233) rDENI/4Δ30, rDEN2/3Δ30, rDEN3/2Δ30, rDEN4Δ30, (234) rDENI/4Δ30, rDEN2/3Δ30, rDEN3/2Δ30, rDEN4/IΔ30, (235) rDENI/4Δ30, rDEN2/3Δ30, rDEN3/2Δ30, rDEN4/2Δ30, (236) rDENI/4Δ30, rDEN2/3Δ30, rDEN3/2Δ30, rDEN4/3Δ30, (237) rDENI/4Δ30, rDEN2/3Δ30, rDEN3/4Δ30, rDEN4Δ30, (238) rDENI/4Δ30, rDEN2/3Δ30, rDEN3/4Δ30, rDEN4/IΔ30, (239) rDENI/4Δ30, rDEN2/3Δ30, rDEN3/4Δ30, rDEN4/2Δ30, (240) rDENI/4Δ30, rDEN2/3Δ30, rDEN3/4Δ30, rDEN4/3Δ30, (241) rDENI/4Δ30, rDEN2/4Δ30, rDEN3Δ30, rDEN4Δ30, (242) rDENI/4Δ30, rDEN2/4Δ30, rDEN3Δ30, rDEN4/IΔ30, (243) rDENI/4Δ30, rDEN2/4Δ30, rDEN3Δ30, rDEN4/2Δ30, (244) rDENI/4Δ30, rDEN2/4Δ30, rDEN3Δ30, rDEN4/3Δ30, (245) rDENI/4Δ30, rDEN2/4Δ30, rDEN3/IΔ30, rDEN4Δ30, (246) rDENI/4Δ30, rDEN2/4Δ30, rDEN3/IΔ30, rDEN4/IΔ30, (247) rDENI/4Δ30, rDEN2/4Δ30, rDEN3/IΔ30, rDEN4/2Δ30, (248) rDENI/4Δ30, rDEN2/4Δ30, rDEN3/IΔ30, rDEN4/3Δ30, (249) rDENI/4Δ30, rDEN2/4Δ30, rDEN3/2Δ30, rDEN4Δ30, (250) rDENI/4Δ30, rDEN2/4Δ30, rDEN3/2Δ30, rDEN4/IΔ30, (251) rDENI/4Δ30, rDEN2/4Δ30, rDEN3/2Δ30, rDEN4/2Δ30, (252) rDENI/4Δ30, rDEN2/4Δ30, rDEN3/2Δ30, rDEN4/3Δ30, (253) rDENI/4Δ30, rDEN2/4Δ30, rDEN3/4Δ30, rDEN4Δ30, (254) rDENI/4Δ30, rDEN2/4Δ30, rDEN3/4Δ30, rDEN4/IΔ30, (255) rDENI/4Δ30, rDEN2/4Δ30, rDEN3/4Δ30, rDEN4/2Δ30, and (256) rDENI/4Δ30, rDEN2/4Δ30, rDEN3/4Δ30, rDEN4/3Δ30.

According to sixth embodiment of the present disclosure, one or more carbohydrates include, but are not limited to, natural carbohydrates, synthetic carbohydrates, polyols, glass transition facilitating agents monosaccharides, disaccharides, trisaccharides, oligosaccharides and their corresponding sugar alcohols, polyhydroxyl compounds such as carbohydrate derivatives and chemically modified carbohydrates, hydroxyethyl starch and sugar copolymers. Both natural and synthetic carbohydrates are suitable for use. Synthetic carbohydrates include, but are not limited to, those which have the glycosidic bond replaced by a thiol or carbon bond. Both D and L forms of the carbohydrates may be used. The carbohydrate may be non-reducing or reducing. Where a reducing carbohydrate is used, the addition of inhibitors of the Maillard reaction is preferred. Reducing carbohydrates suitable for use in the composition are those known in the art and include, but are not limited to, glucose, sucrose, maltose, lactose, fructose, galactose, mannose, maltulose and lactulose. Non-reducing carbohydrates include, but are not limited to, non-reducing glycosides of polyhydroxyl compounds selected from sugar alcohols and other straight chain polyalcohols. Other useful carbohydrates include raffinose, stachyose, melezitose, dextran, cellibiose, mannobiose and sugar alcohols. The sugar alcohol glycosides are preferably monoglycosides, in particular the compounds obtained by reduction of disaccharides such as lactose, maltose, lactulose and maltulose. Glass forming agent is selected from the group consisting of sucrose, mannitol, trehalose, mannose, raffinose, lactitol, lactobionic acid, glucose, maltulose, isomaltulose, maltose, lactose sorbitol, dextrose, fucose or a combination thereof.

Yet according to the preferred aspect of the sixth embodiment, an immunogenic composition comprises of sucrose as suitable carbohydrate stabilizer ranging in between 1% and 20% weight/volume, preferably in between 1-10%, more preferably in between 3-6%, most preferably less than or equal to 5% (w/v).

According to seventh embodiment of the present disclosure, the one or more amino acid include, but are not limited to, leucine, iso-leucine, histidine, glycine, glutamine, arginine, lysine, alanine or a combination of amino acids, peptide, hydrolysed protein or protein such as serum albumin.

Yet according to the preferred aspect of the seventh embodiment, an immunogenic composition comprises of glycine as suitable amino acid stabilizer ranging in between 1% and 20% weight/volume, preferably in between 1-10%, more preferably in between 3-6%, most preferably less than or equal to 5% (w/v).

According to a eighth embodiment of the present disclosure, an immunogenic composition may additionally comprise of a buffering agent selected from the group consisting of carbonate, phosphate, citrate, lactate, gluconate and tartrate buffering agents, as well as more complex organic buffering agents including a phosphate buffering agent that contains sodium phosphate and/or potassium phosphate in a ratio selected to achieve the desired pH. In another example, the buffering agent contains Tris (hydroxymethyl) aminomethane, or "Tris", formulated to achieve the desired pH. Yet in another example, the buffering agent could be the minimum essential medium with Hanks salts.

According to a ninth embodiment of the present disclosure, an immunogenic composition may additionally comprise of preservative selected from the group consisting of 2-phenoxyethanol, Benzethonium chloride (Phemerol), Phenol, m-cresol, Thiomersal, Formaldehyde, methyl and propyl parabens, benzalkonium chloride, benzyl alcohol, chlorobutanol, p-chlor-m-cresol, or benzyl alcohol or a combination thereof.

According to a tenth embodiment of the present disclosure, an immunogenic composition may additionally comprise of pharmaceutically acceptable excipients selected from the group consisting of surfactants, polymers and salts. Examples of Surfactants may include non-ionic surfactants such as polysorbate 20, polysorbate 80, etc. Examples of the polymers may include dextran, carboxymethylcellulose, hyaluronic acid, cyclodextrin, etc. Examples of the salts may include NaCl, MgC12, KCl, CaC12, etc.

According to an eleventh embodiment of the present disclosure, an immunogenic composition may additionally comprise of an adjuvant selected from the group consisting of an aluminum salt, aluminum hydroxide, aluminum phosphate, aluminum hydroxyphosphate, and potassium aluminum sulfate.

According to twelfth embodiment of the present disclosure, an immunogenic composition may additionally comprise of an immunostimulatory component selected from the group consisting of: an oil and water emulsion, MF-59, a liposome, a lipopolysaccharide, a saponin, lipid A, lipid A derivatives, Monophosphoryl lipid A, 3-deacylated monophosphoryl lipid A, AS01, AS03, an oligonucleotide, an oligonucleotide comprising at least one unmethylated CpG and/or a liposome, Freund's adjuvant, Freund's complete adjuvant, Freund's incomplete adjuvant, polymers, co-polymers such as polyoxyethylene-polyoxypropylene copolymers, including block co-polymers, polymer p 1005, CRL-8300 adjuvant, muramyl dipeptide, TLR-4 agonists, flagellin, flagellins derived from gram negative bacteria, TLR-5 agonists, fragments of flagellins capable of binding to TLR-5 receptors, QS-21, ISCOMS, saponin combination with sterols and lipids.

According to thirteenth embodiment of the present disclosure, the said immunogenic composition is lyophilized (freeze-dried).

According to a fourteenth embodiment of the present disclosure, the lyophilized immunogenic composition is stable at 2-8 deg C. from 12 to 36 months; at 25 deg C. from 2 to 6 months; at 37 deg C. from 1 week to 4 weeks, at 42 deg C. for 2-7 days, at 55 deg C. for 2-7 days.

According to fifteenth embodiment of the present disclosure, a method for reconstituting a lyophilized immunogenic composition comprising the step of reconstituting the lyophilized immunogenic composition with an aqueous solution optionally saline or water for injection (WFI).

According to sixteenth embodiment of the present disclosure, the final pH of the immunogenic composition after reconstitution is in the range of pH 6.0 to pH 8.0; more preferably in the range of pH 7.0 to pH 8.0; more preferably in the range of pH 7.2 to pH 7.9; and most preferably in the range of pH 7.5 to pH 7.9.

According to a seventeenth embodiment of the present disclosure, the process for preparing live attenuated chimeric/recombinant tetravalent dengue (DEN) vaccine composition comprises any subset or all of the following steps:

a) Vero cells were revived and adapted to grow in Minimum essential medium (MEM) with Hank's salt solution and 10% Fetal bovine serum
b) Vero cells were initially amplified in tissue culture flasks (TCF with 175 $cm^2$ surface area available for cell growth) producing Master banks and Working banks of Vero cells
c) Cryopreserved cells from the working cell bank were revived, amplified and further passaged in roller bottles (850 $cm^2$ surface area available for cell growth) and incubated at 37±1° C. to obtain monolayers
d) Vero cell monolayers in roller bottles were infected with working seed of dengue virus serotypes 1, 2, 3 and 4
e) All roller bottles were incubated at 34±1° C. for 20 min.; and volume top up to 120 ml per RB using Minimum essential medium (MEM) with Hanks salt solution and 2% Fetal bovine serum. Further all roller bottles were incubated at 34±1° C. for 2 days and 0.7 RPM rolling speed.
f) On day 2, monolayers in roller bottles were washed with fresh virus medium devoid of fetal bovine serum and RBs were incubated at 34±1° C. for 3 days each at 0.7 RPM rolling speed
g) On $5^{th}$ day post infection the cell supernatant from all the infected roller bottles was harvested and bottles re-fed with fresh virus medium devoid of fetal bovine serum;
h) Multiple harvests were taken and processed separately to obtain clarified monovalent virus pools (CMVPs)
i) Filtering the viral harvest by direct flow filtration (DFF) through at least one clarification filter
j) Treating the viral harvest with a non-specific endonuclease to degrade cellular DNA
k) The treated viral harvest was subjected to tangential flow filtration
l) Stabilizing the viral harvest with a stabilizing agent comprising of atleast one amino-acid and atleast one carbohydrateto form a stabilized viral harvest
m) Sterilizing the stabilized viral harvest by DFF through at least one sterilization grade filter
n) Clarified monovalent virus pools (CMVPs) of each of the dengue virus serotype were stored in polycarbonate bottles at −60° C. or below
o) Clarified monovalent virus pools (CMVPs) of all four virus serotypes were mixed together to obtain final bulk which is filled in vials and lyophilized to obtain the drug product i.e recombinant dengue tetravalent vaccine (live attenuated)

According to a first aspect of seventeenth embodiment, the Vero cell line used were ATCC CCL-81 (cGMPVero, Kidney cells derived from African green monkey (*Cercopithecus aeothiops*; available from the ATCC, Manassas, Va., USA)

According to a second aspect of seventeenth embodiment, multiple harvests were carried out at an appropriate time interval for about 4-5 times—more preferably 4 times on $5^{th}$ Day, $7^{th}$ Day, $9^{th}$ Day & $11^{th}$ Day before discarding the input material and processed separately to obtain clarified monovalent virus pools (CMVPs). In case of multiple harvests the same quantity of input material contributes higher yield as compared to conventional single harvest method. This also saves time and total production cost for upstream processing i.e. amplification of cells for infection.

According to a third aspect of seventeenth embodiment, wherein the virus medium comprises of Minimum Essential Medium (MEM) with Hanks salt solution additionally containing Dextrose, L-Glutamine and Sodium Bicarbonate.

According to a fourth aspect of seventeenth embodiment, the medium containing the virus is clarified, typically through filters of decreasing pore sizes (e.g., 6μ, 0.8μ, 0.45μ, 0.2μ). Suitable commercially available filters and filtration devices are well known in the art and can be selected by those of skill. Exemplary filtration devices include, e.g., Millipak (Millipore), Kleenpak (Pall) and Sartobran™ P filtration devices.

According to a fifth aspect of seventeenth embodiment, the filtered harvest was treated with a non-specific endonuclease most preferably Benzonase with concentration varying in between 1-10 units/ml, at temperature ranging in between 4-37° C., and for intervals ranging in between 2 hours to 12 hours.

According to a sixth aspect of seventeenth embodiment, the Benzonase treated harvest was further subjected to tangential flow filtration (TFF) typically through filters with a molecular weight cut off (MWCO) of 500 KD, more preferably 300 KD and most preferably 100 KD.

According to seventh aspect of the seventeenth embodiment, the viral harvest was subjected to tangential flow filtration (TFF) resulting in at least 10×concentration of viral harvest and further results in the removal of residual impurities.

Yet preferable the residual impurities comprises of residual DNA, residual bovine serum albumin (BSA) and residual host cell protein.

According to eighth aspect of the seventeenth embodiment, the process described above result in a purified and concentrated flavivirus preparation more preferably dengue virus preparation wherein, the preparations comprises of concentrated live attenuated dengue virus particles, traces of residual cellular DNA (<10 ng/dose), residual BSA (<50 ng/dose) and residual cellular proteins. Furthermore, according to the process described above, the overall recovery of purified viruses is at least 50%.

According to ninth aspect of the seventeenth embodiment, stabilizers comprising solution of one or more amino-acid and one or more carbohydrate were mixed with concentrated virus stock (TFF concentrate) in 60:40 or 50:50 or 40:60 proportion of virus stock to stabilizer to obtain the final formulation.

Yet preferable the stabilizers comprising solution of sucrose at a concentration of 7.5 to 15% (w/v) and glycine at a concentration of 7.5 to 15% (w/v) were mixed with concentrated virus stock (TFF concentrate) in 60:40 or 50:50 or 40:60 proportion of virus stock to stabilizer to obtain the final formulation comprising sucrose at a concentration of 3 to 6% (w/v) and glycine at a concentration of 3 to 6% (w/v).

Yet preferable the stabilizers comprising solution of sucrose at a concentration of 12.5% (w/v) and glycine at a concentration of 12.5% (w/v) were mixed with concentrated virus stock (TFF concentrate) in 60:40 proportion of virus stock to stabilizer to obtain the final formulation comprising sucrose at a concentration of 5% (w/v) and glycine at a concentration of 5% (w/v).

Yet preferable the stabilizers comprising solution of sucrose at a concentration of 11.25% (w/v) and glycine at a concentration of 12.5% (w/v) were mixed with concentrated virus stock (TFF concentrate) in 60:40 proportion of virus stock to stabilizer to obtain the final formulation comprising sucrose at a concentration of 4.5% (w/v) and glycine at a concentration of 5% (w/v).

Yet preferable the stabilizers comprising solution of sucrose at a concentration of 15% (w/v) and glycine at a concentration of 15% (w/v) were mixed with concentrated virus stock (TFF concentrate) in 60:40 proportion of virus stock to stabilizer to obtain the final formulation comprising sucrose at a concentration of 6% (w/v) and glycine at a concentration of 6% (w/v).

According to tenth aspect of seventeenth embodiment, the multiplicity of infection (MOI) of flavivirus more preferably dengue virus to obtain master seed and working seed is in the range 0.01 to 0.1 for each dengue serotype.

Yet preferably the multiplicity of infection (MOI) of dengue virus to obtain master seed and working seed is 0.01.

According to a eleventh aspect of seventeenth embodiment, the immunogenic composition comprises flavivirus more preferably dengue virus at a dose of not less than 2.5 $\log_{10}$ PFU per 0.5 ml of each of dengue virus serotype 1, 2, 3 and 4 According to a twelfth aspect of seventeenth embodiment, the immunogenic composition comprises dengue virus at a dose of log $10^3$ to log $10^5$ PFU per 0.5 ml, more preferably log $10^3$ to log $10^4$ PFU/per 0.5 ml, most preferably log $10^3$ PFU/per 0.5 ml of each of dengue virus serotype 1, 2, 3 and 4.

According to an eighteenth embodiment of the present disclosure, the method of lyophilization (freeze-drying) of an immunogenic composition comprises the steps of freezing, primary drying and secondary drying.

Yet preferably the method of lyophilization (freeze-drying) of live attenuated chimeric/recombinant tetravalent dengue (DEN) vaccine composition comprises any subset or all of the following steps:

a) Product loading at temperatures between 20 to 5° C.

b) Stepwise freezing with holding time at each temperature, wherein freezing step comprises of freezing at about −30° C. to −45° C. at a freezing rate of 0.5 to 1° C./min from about 60 minutes to 930 minutes c) Annealing at −20° C. for 5 hrs followed by freezing at −45° C.

d) Primary drying comprises stepwise ramping of temperature at about 0.5° C./minute to 1.0° C./minute to achieve shelf temperature of about −25° C. to −32° C. holding for about 600 minutes to 1980 minutes under pressure of about 55 pbar;

e) Secondary drying involve heating product at the rate of 0.5 to 1.0° C./min, to achieve shelf temperature of about 25° C. to 30° C. holding for about 360 minutes to 600 minutes under pressure of 55 pbar.

The total duration of the lyophilization cycle comprises from about 48 hours to 56 hours. Variations in temperature and cycle duration as per vial specification and lyophilizer design are contemplated. The product is lyophilized based on a pre-determined cycle to achieve a target moisture content of about 2.0% w/w to 3.5% w/w.

As used herein the terms "Freeze-drying" or "lyophilize" or "lyophilization" involves lyophilization and refers to the process by which a suspension is frozen, after which the water is removed by sublimation at low pressure. As used herein, the term "sublimation" refers to a change in the physical properties of a composition, wherein the composition changes directly from a solid state to a gaseous state without becoming a liquid.

According to a nineteenth embodiment of the present disclosure, the immunogenic composition is formulated for use in a method for reducing the onset of or preventing a health condition involving administration of an effective amount of the immunogenic composition to a human subject via intramuscular, or intravenous, subcutaneous, or transcutaneous or intradermal.

According to a twentieth embodiment of the present disclosure, the health condition is selected from the group consisting of Dengue virus infection, Zika virus infection, West Nile infection, Japanese encephalitis infection, Kunjin virus infection, tick-borne encephalitis infection, St. Louis encephalitis virus infection, Murray Valley encephalitis virus infection, yellow fever virus infection.

According to a twenty first embodiment of the present disclosure, the immunogenic composition may be administered subcutaneously, intradermally, or intramuscularly in a dose effective for the production of neutralizing antibody and protection. The vaccines are administered in a manner compatible with the dosage formulation, and in such amount as will be prophylactically and/or therapeutically effective. The immunogenic composition of the present disclosure can be administered as primary prophylactic agents in adults or children at the risk of infection, or can be used as secondary agents for treating infected patients. For example, the live attenuated dengue (DEN) tetravalent vaccine composition as disclosed herein can be used in adults or children at risk of dengue virus infection, or can be used as secondary agents for treating DEN virus infected patients.

According to a twenty second embodiment of the present disclosure, the immunogenic composition can be formulated as single dose vials, multidose vials or as pre-filled syringes wherein the said immunogenic composition may be given in a single dose schedule, or preferably a multiple dose schedule in which a primary course of vaccination may be with 1-2 separate doses, followed by other doses given at subsequent time intervals required to maintain and or reinforce the immune response, for example, at 1-4 months for a second dose, and if needed, a subsequent dose(s) after several months or years. The dosage regimen will also, at least in part, be determined on the need of a booster dose required to confer protective immunity.

Other embodiments disclosed herein also encompasses vaccine kit comprising a first container containing a lyophilized (freeze-dried) immunogenic composition and a second container containing an aqueous solution optionally saline or WFI (water for injection) for the reconstitution of the lyophilized (freeze-dried) immunogenic composition.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

Throughout this specification the word, "immunogenic composition" covers any composition that elicits an immune response against the antigen or immunogen of interest expressed from vectors; for instance, after administration into a subject, elicits an immune response against the targeted immunogen or antigen of interest.

The terms "vaccine composition" and "vaccine" covers any composition that induces a protective immune response against the antigen of interest, or which efficaciously protects against the antigen; for instance, after administration or injection into the subject, elicits a protective immune response against the targeted antigen or immunogen or provides efficacious protection against the antigen or immunogen expressed from vectors.

The use of the expression "at least" or "at least one" suggests the use of one or more elements or ingredients or quantities, as the use may be in the embodiment of the invention to achieve one or more of the desired objects or results. While certain embodiments of the inventions have been described, these embodiments have been presented by way of example only, and are not intended to limit the scope of the inventions. Variations or modifications to the formulation of this invention, within the scope of the invention, may occur to those skilled in the art upon reviewing the disclosure herein. Such variations or modifications are well within the spirit of this invention.

The numerical values given for various physical parameters, dimensions and quantities are only approximate values and it is envisaged that the values higher than the numerical value assigned to the physical parameters, dimensions and quantities fall within the scope of the invention unless there is a statement in the specification to the contrary.

Similarly, the components used in purification, e.g., filters, columns, are not intended to be in any way limiting or exclusionary, and can be substituted for other components to achieve the same purpose at the discretion of the practitioner.

While considerable emphasis has been placed herein on the specific features of the preferred embodiment, it will be appreciated that many additional features can be added and that many changes can be made in the preferred embodiment without departing from the principles of the disclosure. These and other changes in the preferred embodiment of the disclosure will be apparent to those skilled in the art from the disclosure herein, whereby it is to be distinctly understood that the foregoing descriptive matter is to be interpreted merely as illustration of the disclosure and not as a limitation.

Advantages

The present disclosure described herein above has several technical advances and advantages including, but not limited to, the realization of a stable lyophilized immunogenic composition comprising live attenuated recombinant dengue viruses, atleast one carbohydrate, atleast one amino acid and the method of manufacturing the same. When compared to other lyophilized immunogenic composition, the present disclosure provides the following advantages:

1. Minimum components involved in the vaccine composition.

2. The reconstituted vaccine preserves desired characteristics of a virus including virus viability, immunogenicity and stability.

3. Improved stability at 2-8° C., 25° C., 37° C., 42@C and 55° C. for an extended period.

4. Devoid of preservatives, polymers and surfactants.

5. Improved method of manufacturing such stable composition/formulation that result in improved yield. Examples:

The following examples are included to demonstrate preferred embodiments of the invention. It should be appreciated by those of skill in the art that the compositions and techniques disclosed in the examples which follow represent techniques discovered by the inventor to function well in the practice disclosed herein, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Multiple Harvesting vs. Single Harvest

Certain experiments were performed to initially identify the method of manufacturing the immunogenic composition suitable for preclinical and clinical testing and use of flavivirus immunogenic compositions or vaccines were identified. In some exemplary methods, live, attenuated recombinant/chimeric dengue viruses were used as an exemplary flaviviruses in various compositions for pre-clinical and clinical testing. The candidate dengue vaccine strains were supplied by National Institute of Health (NIH), USA.

The process for manufacturing live attenuated chimeric/recombinant tetravalent dengue (DEN) vaccine composition comprises any subset or all of the following steps:

1. Vero cells were revived and adapted to grow in Minimum essential medium (MEM) with Hanks salt solution and 10% Fetal bovine serum (FBS);
2. Vero cells were initially amplified in tissue culture flasks (TCF with 175 $cm^2$ surface area available for cell growth) producing Master banks and Working banks of Vero cells.
3. Cryopreserved cells from the working cell bank were revived, amplified and further passaged in roller bottles (RBs) (850 $cm^2$ surface area available for cell growth) and incubated at 37±1° C. & 0.7 RPM rolling speed to obtain monolayers.
4. Vero cell monolayers in roller bottles were infected with working seed of dengue virus serotypes 1, 2, 3 and 4 at 0.01 MOI
5. All roller bottles were incubated at 34±1° C. for 20 min.; and volume top up to 120 ml per RB using Minimum essential medium (MEM) with Hanks salt solution and 2% Fetal bovine serum. Further all roller bottles were incubated at 34±1° C. for 2 days and 0.7 RPM rolling speed.
6. On day 2 monolayers in roller bottles were washed with fresh virus medium devoid of fetal bovine serum to remove traces of FBS and were incubated at 34±1° C. & 0.7 RPM rolling speed for 3 days.
7. On $5^{th}$ day post infection the cell supernatant from all the infected roller bottles was harvested and bottles re-fed with fresh virus medium comprising MEM with Hanks salt solution additionally containing Dextrose, L-Glutamine and Sodium Bicarbonate and is devoid of fetal bovine serum;

TABLE 3

| Composition of Minimum Essential Medium with Hank's salt | |
|---|---|
| Component | MG/L |
| Calcium Chloride (Anhydrous) | 140 |
| Magnesium Sulphate (Anhydrous) | 98 |
| Potassium Chloride | 400 |
| Potassium Phosphate Monobasic (Anhydrous) | 60 |
| Sodium Chloride | 8000 |
| Sodium Phosphate Dibasic (Anhydrous) | 48 |
| L-Arginine HCl | 126 |
| L-Cystine HCl | 31 |
| L-Glutamine | 292 |

TABLE 3-continued

| Composition of Minimum Essential Medium with Hank's salt | |
|---|---|
| Component | MG/L |
| L-Histidine HCl H20 | 42 |
| L-Isoleucine | 52 |
| L-Leucine | 52 |
| L-Lysine HCl | 73 |
| L-Methionine | 15 |
| L-Phenylalanine | 32 |
| L-Threonine | 48 |
| L-Tryptophan | 10 |
| L-Tyrosine 2NA 2H2O | 52 |
| L-Valine | 46 |
| Choline Chloride | 1 |
| Folic Acid | 1 |
| I-Inositol | 2 |
| Niacinamide | 1 |
| D-Panthothenic Acid (Hemicalcium) | 1 |
| Pyridoxal HCl | 1 |
| Riboflavin | 0.1 |
| Thiamine HCl | 1 |
| Glucose | 1000 |
| Phenol Red | 10 |

Various approaches for harvesting of dengue virus were carried out as single harvest and multiple harvests at various time points (from day4 to day12 after infection) as daily, on odd days, on even days etc. The comparison of virus titers with respect to yields by single harvest versus multiple harvests was conducted.

TABLE 4

| Harvesting Time Points | | |
|---|---|---|
| Set No. | No. of RBs | Harvest/Sampling Details |
| 1 | 3 | Daily harvest on 4, 5, 6, 7, 8, 9 days |
| 2 | 3 | Even day harvest on 4, 6, 8 days |
| 3 | 3 | Odd day harvest on 5, 7, 9, 11 days. |
| 4 | 3 | Daily sampling on 4, 5, 6, 7, 8, 9, 10, 11 days |
| 5 | 3 | Single harvest on day 6 |
| 6 | 3 | Single harvest on day 7 |

From day 4, the infected RBs were harvested set wise (set 1 to 4) on respective days. After harvesting, the RBs were re-fed with fresh virus medium-VM, and incubated at 34° C. till next harvest. Also a single harvest of supernatant was collected on day 6 (set 5) & day 7 (set 6) respectively.

These samples were tested for virus titers ($CCID_{50}$) by Spearman Karber method.

TABLE 5

| DEN 1 Virus Titers(CCID50) | | | | | |
|---|---|---|---|---|---|
| | DEN 1 Virus Titers ($CCID_{50}$/ml) | | | | |
| Harvest Days | Odd Day | Even Day | Daily | Single Harvest | Growth Curve |
| Day 4 | | 5.5 | 5.5 | | 6 |
| Day 5 | 6.125 | | 6.375 | | 6.3 |
| Day 6 | | 6.625 | 6.375 | 6.975 | 7 |
| Day 7 | 7.375 | | 7 | 7.1 | 7.25 |
| Day 8 | | 7.125 | 6.625 | | 7.625 |
| Day 9 | 7.25 | | 6.5 | | 7 |
| Day 10 | | 6.5 | 6.125 | | 6.875 |
| Day 11 | 6.25 | | 6.5 | | 7 |
| Day 12 | | | | | 6.25 |

The growth curve obtained with Dengue Virus Serotype 1 (DEN 1) showed that multiple harvesting on day 5, 7, 9 & 11 gave good virus titers and hence would be the choice for further batches (Refer FIG. 4).

One more trial on multiple harvests versus single harvest was conducted using 18 RBs for Den 2, 3 & 4.

TABLE 6

| DEN 2, 3, 4 Virus Titers ($CCID_{50}$) | | | | |
|---|---|---|---|---|
| | Harvest | Virus Titers ($CCID_{50}$/ml) | | |
| | Days | DEN 2 | DEN 3 | DEN 4 |
| Multiple Harvest | Day 5 | 6.621 | 5.825 | 7.432 |
| | Day 7 | 6.73 | 6.021 | 7.588 |
| | Day 9 | 6.485 | 5.76 | 7.67 |
| | Day 11 | 6.202 | 5.64 | 7.321 |
| Single Harvest | Day 6 | 6.691 | 5.882 | 7.575 |

Refer Figure-5 for Log Yield Titers of DEN 2, 3, 4 Virus using 90 roller bottles (Multiple Harvest vs. Single Harvest)

The cumulative yield of multiple harvests from single batch was much higher (around 0.4 to 0.6 log) than yield obtained by single harvest. As 0.3 log is equivalent to double of absolute value; this difference is more significant. Thus, the approach of multiple harvesting is more beneficial and preferred over single harvest.

Example 2

Dengue virus is grown on Vero cells. Thus it is required to remove impurity from the harvest. Impurities like Host cell DNA is treated with Benzonase.

Effect of Benzonase Concentration and Temperature on Cellular DNA Content and Virus Titer 1. Multiple harvests were taken and processed separately to obtain clarified monovalent virus pools (CMVPs).
2. These multiple harvests are clarified through 6μ+0.45μ filter and treated with Benzonase to degrade cellular DNA.
3. Various experiments were performed to identify the ideal Benzonase concentration and temperature for treating harvest.

In this experiment Benzonase was added at four different concentration 500 units/liter, 1250 units/liter, 2500 units/liter and 5000 units/liter at 34±1° C. for 2 hours. It was observed that at 1250, 2500 and 5000 units/liter concentration of Benzonase, there was optimum degradation of DNA. Based on results 1250 units/liter was selected as working concentration.

TABLE 7

| Effect of Benzonase concentration on DNA content (ng/ml) | | | | | |
|---|---|---|---|---|---|
| | Control | 500 U/L | 1250 U/L | 2500 U/L | 5000 U/L |
| Day 5 | 127 | 54 | 5 | 6 | 4 |
| Day 7 | 310 | 36 | 7 | 9 | 3 |
| Day 9 | 169 | 19 | 2 | 1 | 5 |

Refer FIG. 6: Effect of Benzonase Concentration on DNA Content

Refer FIG. 7: Effect of Temperature on Cellular DNA Content and Virus Titer

The dengue virus is sensitive to long time of temperature exposure so short period of exposure was used in the experiment i.e 2 hours at different temperature. It was observed that there was loss in titer at 37° C. while DNA content was low. At 34° C. there was no loss in virus titer and DNA content was low. While at 25° C. and 2 to 8° C. there was no loss in virus titer as well as DNA degradation was also less. Thus 34° C. was selected for process.

Example 3: Filtration & Concentration

1. Dengue viruses are grown on Vero cells. Thus it is required to remove impurity from the harvest.
2. Impurities like Host cell DNA, host cell protein, residual BSA and residual Benzonase.
3. Tangential flow filtration (TFF) is a process which we used to remove these impurities.
4. Benzonase treated harvest is subjected to TFF for removal of impurities.

In the initial experiments TFF was done using Millipore V screen cassette of 300 KD and Pall T series 300 KD. It was observed that there is virus loss of ≥3.5 log in permeate. Thus it was planned to change the cassette size to 100 KD. During these experiments it was observed that in Millipore cassette there was no virus in permeate.

After doing various trials of TFF based on results, 100 KD V screen Merck Millipore cassettes with only 10×concentration process which gave us desirable product. Virus is concentrated to reduce the requirement of storage space for bulk vaccine and removal of impurities. Based on below table it is clear that there was no significant loss in virus titer and significant removal of Host cell DNA after Benzonase treatment and TIFF.

TABLE 8

| Host Cell DNA Concentration in ng/ml | | | |
|---|---|---|---|
| Intermediate Stage | Day of harvest | | |
| of Production | 5 | 7 | 9 |
| DEN 1 | | | |
| CVP | 1754.5 | 2255.9 | 1631.2 |
| BCVP | 186.42 | 98.813 | 88.201 |
| CMVP | 2.238 | 3.583 | 4.134 |
| DEN 2 | | | |
| CVP | 2430.3 | 2160.1 | 2419.215 |
| BCVP | 215.809 | 176.026 | 95.958 |
| CMVP | 15.285 | 8.236 | 6.409 |
| DEN 3 | | | |
| CVP | 1578.6 | 1340.3 | 522.7 |
| BCVP | 93.877 | 22.9 | 10.37 |
| CMVP | 4.564 | 4.07 | 3.43 |
| DEN 4 | | | |
| CVP | 1283.1 | 350.8 | 110.1 |
| BCVP | 30.19 | 53.14 | 26.81 |
| CMVP | 7.22 | 5.93 | 8.13 |

CVP: Clarified virus pool (harvest post filtration)

BCVP: CVP treated with Benzonase

CMVP: Clarified monovalent virus pool (post TIFF, addition of stabilizer and post 0.2μ filtration)

TABLE 9

| Host cell DNA in final product | | |
|---|---|---|
| Sr. No. | Batch No. | DNA (ng/dose) |
| 1 | Batch 1 | 0.345 |
| 2 | Batch 2 | 0.043 |
| 3 | Batch 3 | 0.580 |

TABLE 10

| Mean Virus recovery in 3 consecutive batches (%) | | | | |
|---|---|---|---|---|
| Serotype | Batch 1 | Batch 2 | Batch 3 | Mean recovery |
| DEN 1 | 88.6 | 92.4 | 87.1 | 89.4 |
| DEN 2 | 99.1 | 96.8 | 94.7 | 96.9 |
| DEN 3 | 88.4 | 94.6 | 89.2 | 90.7 |
| DEN 4 | 98.9 | 101.4 | 90.2 | 96.8 |

Study of Various Stabilizers and Optimization of Stabilizer Formulation

Stability of live, attenuated flavivirus immunogenic compositions were tested as a function of potency loss using various stabilizing formulations (e.g., titer loss or $Log_{10}$ PFU/dose).

Dengue monovalent bulks were formulated using different stabilizer combinations as illustrated in table 11 and 12. The principal components of these stabilizers were Gelatin, Sorbitol, Sucrose, Glycine, Phosphates ($KH_2PO_4$, $K_2HP_4$), Glutamate, Lactalbumin hydrolysate (LAH) and amino acids as L-Histidine, L-Arginine hydrochloride, L-Alanine, Tricine etc.

TABLE 11

| Various Stabilizer Combinations | |
|---|---|
| No. | Composition of stabilizer |
| A | Gelatin 2% + Sucrose 20% + Amino acids (2×) |
| B | Gelatin 2% + Sucrose 10% + Amino acids (2×) |
| C | Gelatin 2% + LAH 0.70% + Sucrose 20% + Amino acids (2×) |
| D | Sucrose-Phosphate-Glutamate (2×) + LAH 4% + Glycine 10% + Amino acids (2×) |
| E | Gelatin 12.5% − Sorbitol 25% + Stabilizer-II − Mixing proportion 80:20:10 |
| F | Gelatin 12.5% − Sorbitol 25% + Stabilizer-II − Mixing proportion 1:1 |
| G | Sucrose 12.5% w/v + Glycine 12.5% w/v (60:40) |

Stabilizer-II contains L-Histidine (2.1%), L-Alanine 1%, Tricine (3%), L-Arginine hydrochloride (16%), Lactalbumin hydrolysate (3.5%).

The obtained volume of TFF Viral conc. was stabilized using different stabilizer combination as described below:

TABLE 12

| Final Formulation | |
|---|---|
| No. | Formulation |
| A | 50 ml TFF Conc. + 50 ml Stabilizer A (2×) = 100 ml |
| B | 50 ml TFF Conc. + 50 ml Stabilizer B (2×) = 100 ml |
| C | 50 ml TFF Conc. + 50 ml Stabilizer C (2×) = 100 ml |
| D | 50 ml TFF Conc. + 50 ml Stabilizer D (2×) = 100 ml |
| E | 320 ml TFF Conc. + 120 ml Stabilizer E = 440 ml |
| F | 50 ml TFF Conc. + 50 ml Stabilizer F (2×) = 100 ml |
| Lyo 1 | 320 ml TFF Conc. + 120 ml Stabilizer E = 440 ml |
| Lyo 2 | 50 ml TFF Conc. + 33 ml Stabilizer G = 83 ml |

All these formulations were subjected for thermal stability study at 37° C. for 7 days. The samples were tested for infectivity titers by $CCID_{50}$, intermittently at 0, 1, 3, 5 & 7 days.

The results of infectivity titers of the various liquid formulations showed significant drop followed by complete loss (after 1 to 5 days) in respective dengue virus titers.

This failure of liquid formulation to retain stability prompted to attempt for lyophilized formulations. The dengue monovalent bulks containing Gelatin+Sorbitol+Stabilizer II (Stabilizer E) were lyophilized and subjected for thermal stability study at 37° C. for 7 days. Samples were tested for infectivity titers by $CCID_{50}$, intermittently at 0, 1, 3, 5 & 7 days. Results of infectivity titers showed better stability profile as compared to liquid formulations and significantly retained the virus titers. Thus, the approach of lyophilization of dengue monovalent formulation successfully overcame the problem of poor stability & found significant reduction of loss in virus titers.

Also another StabilizerG comprising of Sucrose+Glycine was tried out; and was excellent in form of lyophilized formulation for all four dengue viruses. Samples were tested for infectivity titers by $CCID_{50}$, intermittently at 0, 1, 3, 5 & 7 days. Results of infectivity titers showed better stability profile as compared to other stabilizers e.g. Gelatin+Sorbitol+stabilizer II. Also, it is easy to prepare and use; since it is sourced from non-animal origin.

TABLE 13

| DEN 1 Titer $CCID_{50}$/ml (Liquid vs. Lyophilized) | | | | | | | | |
|---|---|---|---|---|---|---|---|---|
| Storage time | A | B | C | D | E | F | LYO 1 | LYO 2 |
| 0 | 7.21 | 7.35 | 7.07 | 7.07 | 7.21 | 7.21 | 5.78 | 5.62 |
| 1 | 5.21 | 4.07 | 4.07 | 4.78 | 2.78 | 2.78 | 5.78 | 5.59 |
| 3 | 2.92 | 2.78 | 0 | 2.64 | 2.64 | 2.64 | 5.35 | 5.46 |
| 5 | 0 | 0 | 0 | 0 | 0 | 0 | 4.78 | 5.31 |
| 7 | — | — | — | — | — | — | 4.64 | 5.18 |

Refer FIG. 8: DEN-1 titer $CCID_{50}$/ml (Liquid vs. Lyophilized)

TABLE 14

| DEN 2 Titer $CCID_{50}$/ml (Liquid vs. Lyophilized) | | | | | | |
|---|---|---|---|---|---|---|
| Storage time | A | B | C | D | LYO 1 | LYO 2 |
| 0 | 5.625 | 5.75 | 4.88 | 5 | 4.64 | 4.7 |
| 1 | 0 | 0 | 0 | 0 | 4.21 | 4.52 |
| 3 | — | — | — | — | 4.07 | 4.43 |
| 5 | — | — | — | — | 3.75 | 4.26 |
| 7 | — | — | — | — | 3.5 | 4.15 |

Refer FIG. 9: DEN 2 Titer $CCID_{50}$/ml (Liquid vs. Lyophilized)

TABLE 15

| DEN 3 Titer $CCID_{50}$/ml (Liquid vs. Lyophilized) | | | | | | | |
|---|---|---|---|---|---|---|---|
| Storage time | A | B | C | D | F | LYO 1 | LYO 2 |
| 0 | 6.92 | 7.07 | 6.35 | 6.92 | 6.78 | 6.83 | 6.76 |
| 1 | 4.21 | 4.92 | 3.6 | 4.07 | 0 | 6.69 | 6.65 |
| 3 | 0 | 0 | 0 | 0 | NT | 6.58 | 6.56 |
| 5 | NT | NT | NT | NT | NT | 6.43 | 6.44 |
| 7 | NT | NT | NT | NT | NT | 6.35 | 6.33 |

NT-Not tested

Refer FIG. 10: DEN-3 Titer $CCID_{50}$/ml (Liquid vs. Lyophilized)

TABLE 16

| DEN 4 Titer $CCID_{50}$/ml (Liquid vs. Lyophilized) | | |
|---|---|---|
| Storage time | LYO 1 | LYO 2 |
| 0 | 4.64 | 4.78 |
| 1 | 4.64 | 4.75 |

TABLE 16-continued

| DEN 4 Titer $CCID_{50}$/ml (Liquid vs. Lyophilized) | | |
|---|---|---|
| Storage time | LYO 1 | LYO 2 |
| 3 | 4.64 | 4.74 |
| 5 | 4.25 | 4.57 |
| 7 | 3.87 | 4.32 |

Refer FIG. 11: DEN 4 Titer $CCID_{50}$/ml (Lyophilized)

With reference to all above results of stability study, the better stability profile was obtained with LYO 2 (Sucrose & Glycine). Hence, the stabilizer composition of Sucrose & Glycine was further optimized to get more stable formulation.

Example 5

Lyophilization Conditions

For dengue vaccine development initially we have tried various different stabilizers formulations for liquid vaccine, but it was found that virus does not remain stable in liquid formulation and there was significant titer loss with liquid formulation within 5 days stored at 37° C. Liquid formulation doesn't work for dengue vaccine. So we further decided to carry out next trials of dengue vaccine bulk using lyophilisation.

Different lyophilisation trials were planned and carried out on Dengue monovalent as well as tetravalent bulk to study suitability of stabilizer for vaccine formulation and stability of all four virus serotypes in tetravalent mixture during storage at low temperature.

Our study trials showed that virus remains more stable in lyophilized form than in liquid form and no virus titer loss was observed after lyophilisation as illustrated in example 4.

We opted for lyophilized form dengue vaccine to obtain better stability of the product. Lyophilisation trials were carried out by using Dengue CMVP-bulk containing Gelatin-Sorbitol or Sucrose-Glycine as stabilizers as illustrated in example 4. As gelatin is of porcine origin and nowadays there are some ethical issues for its use in vaccine. Also complexity in its preparation which requires hydrolysis of gelatin at high temperature. With use of Gelatin-Sorbitol stabilizer no consistency in infectivity titers of all four serotypes and considerable virus loss was observed from thawing to lyophilisation step.

After some lyophilisation trials of dengue bulk with Gelatin+sorbitol+stabilizer II we shifted to Sucrose+Glycine as illustrated in example 4 and the lyophilisation trials showed better virus stability for LYO 2 formulation as compared to LYO 1 formulation.

TABLE 17

| Lyophilization Cycle Optimization | | | |
|---|---|---|---|
| Trial No. | Lyo. cycle in Hours. | Titre Loss (pfu/ml) | Moisture content (w/v %) |
| 1 | 43 Hrs. | 0.056 | 2.761 |
| 2 | 42 Hrs. | 0.089 | 3.280 |
| 3 | 27 Hrs. | +0.017 | 3.343 |
| 4 | 35 Hrs. | 0.292 | 3.098 |
| 5 | 39 Hrs. | 0.154 | 2.575 |
| 6 | 45 Hrs. | 0.282 | 2.814 |
| 7 | 56 Hrs. | 0 | 2.495 |

In Trial No. 1 to 7 lyophilization cycle duration was changed from standard cycle of 56 Hrs. The reduction in the hours of lyophilization cycle had an effect on titer loss and moisture content. There was no major loss in virus titer however; moisture content increased from 2.50% to 3.34% w/w as there was reduction in the cycle time. Hence, the lyophilization cycle duration was set around 56 Hrs.

TABLE 18

| Lyophilization process parameters | |
|---|---|
| Activity | Parameters |
| Freezing | −45° C. for 13.5 ± 2 hrs |
| Condenser cooling | ≤1 hrs |
| Chamber Evacuation | ≤1.30 hrs |
| Primary drying | −45° C. to 25° C. for 33 ± 3 hrs |
| Secondary drying | 25° C. for 8 ± 0.5 hrs |

Refer FIG. 12: Lyophilization Cycle

Example 6: Stability Data Post Lyophilization of Dengue Virus Monovalent Bulk at 37±1° C. for 14 Days Dengue virus monovalent bulks (DEN 1, 2, 3, 4) were formulated with varying concentrations of sucrose and glycine to obtain the final formulation comprising concentration of sucrose and glycine as enclosed in table 19 (SG1, SG2, SG3, SG4, SG5, SG6). The stabilized monovalent formulations were lyophilized using standard lyophilization protocol. All lyophilized monovalent and tetravalent dengue virus formulations as enclosed in table below were subjected to thermal stability study at 37±1° C. for 14 days. The samples were collected at respective time points and tested for infectivity titers.

TABLE 19

| Sucrose + Glycine Formulations | | |
|---|---|---|
| Formulation code | Sucrose | Glycine |
| SG1 | 5% w/v | 3% w/v |
| SG2 | 3% w/v | 5% w/v |
| SG3 | 5% w/v | 5% w/v |
| SG4 | 10% w/v | 7% w/v |
| SG5 | 4.5% w/v | 5% w/v |
| SG6 | 6% w/v | 6% w/v |

TABLE 20A

| Dengue Monovalent Vaccine Composition SG1 | |
|---|---|
| Component | Quantity per dose of 0.5 ml |
| Dengue virus serotype 1 (rDEN 1Δ30) | NLT $log_{10}$ 2.5 PFU |
| Sucrose | 5% w/v |
| Glycine | 3% w/v |

TABLE 20B

| Dengue Monovalent Vaccine Composition SG2 | |
|---|---|
| Component | Quantity per dose of 0.5 ml |
| Dengue virus serotype 1 (rDEN 1Δ30) | NLT $log_{10}$ 2.5 PFU |
| Sucrose | 3% w/v |
| Glycine | 5% w/v |

TABLE 20C

| Dengue Monovalent Vaccine Composition SG3 | |
|---|---|
| Component | Quantity per dose of 0.5 ml |
| Dengue virus serotype 1 (rDEN 1Δ30) | NLT $log_{10}$ 2.5 PFU |
| Sucrose | 5% w/v |
| Glycine | 5% w/v |

TABLE 20D

| Dengue Monovalent Vaccine Composition SG4 | |
|---|---|
| Component | Quantity per dose of 0.5 ml |
| Dengue virus serotype 1 (rDEN 1Δ30) | NLT $log_{10}$ 2.5 PFU |
| Sucrose | 10% w/v |
| Glycine | 7% w/v |

TABLE 20E

| Dengue Monovalent Vaccine Composition SG5 | |
|---|---|
| Component | Quantity per dose of 0.5 ml |
| Dengue virus serotype 1 (rDEN 1Δ30) | NLT $log_{10}$ 2.5 PFU |
| Sucrose | 4.5% w/v |
| Glycine | 5% w/v |

TABLE 20F

| Dengue Monovalent Vaccine Composition SG6 | |
|---|---|
| Component | Quantity per dose of 0.5 ml |
| Dengue virus serotype 1 (rDEN 1Δ30) | NLT $log_{10}$ 2.5 PFU |
| Sucrose | 6% w/v |
| Glycine | 6% w/v |

TABLE 21A

| Dengue Monovalent Vaccine Composition SG1 | |
|---|---|
| Component | Quantity per dose of 0.5 ml |
| Dengue virus serotype 2 (rDEN 2/4Δ30) | NLT $log_{10}$ 3.0 PFU |
| Sucrose | 5% w/v |
| Glycine | 3% w/v |

TABLE 21B

| Dengue Monovalent Vaccine Composition SG2 | |
|---|---|
| Component | Quantity per dose of 0.5 ml |
| Dengue virus serotype 2 (rDEN 2/4Δ30) | NLT $log_{10}$ 3.0 PFU |
| Sucrose | 3% w/v |
| Glycine | 5% w/v |

TABLE 21C

| Dengue Monovalent Vaccine Composition SG3 | |
|---|---|
| Component | Quantity per dose of 0.5 ml |
| Dengue virus serotype 2 (rDEN 2/4Δ30) | NLT $log_{10}$ 3.0 PFU |
| Sucrose | 5% w/v |
| Glycine | 5% w/v |

TABLE 21D

| Dengue Monovalent Vaccine Composition SG4 | |
|---|---|
| Component | Quantity per dose of 0.5 ml |
| Dengue virus serotype 2 (rDEN 2/4Δ30) | NLT $log_{10}$ 2.5 PFU |
| Sucrose | 10% w/v |
| Glycine | 7% w/v |

TABLE 21E

| Dengue Monovalent Vaccine Composition SG5 | |
|---|---|
| Component | Quantity per dose of 0.5 ml |
| Dengue virus serotype 2 (rDEN 2/4Δ30) | NLT $log_{10}$ 2.5 PFU |
| Sucrose | 4.5% w/v |
| Glycine | 5% w/v |

TABLE 21F

| Dengue Monovalent Vaccine Composition SG6 | |
|---|---|
| Component | Quantity per dose of 0.5 ml |
| Dengue virus serotype 2 (rDEN 2/4Δ30) | NLT $log_{10}$ 2.5 PFU |
| Sucrose | 6% w/v |
| Glycine | 6% w/v |

TABLE 22A

| Dengue Monovalent Vaccine Composition SG1 | |
|---|---|
| Component | Quantity per dose of 0.5 ml |
| Dengue virus serotype 3 (rDEN 3Δ30/31) | NLT $log_{10}$ 2.5 PFU |
| Sucrose | 5% w/v |
| Glycine | 3% w/v |

TABLE 22B

| Dengue Monovalent Vaccine Composition SG2 | |
|---|---|
| Component | Quantity per dose of 0.5 ml |
| Dengue virus serotype 3 (rDEN 3Δ30/31) | NLT $log_{10}$ 2.5 PFU |
| Sucrose | 3% w/v |
| Glycine | 5% w/v |

TABLE 22C

| Dengue Monovalent Vaccine Composition SG3 | |
|---|---|
| Component | Quantity per dose of 0.5 ml |
| Dengue virus serotype 3 (rDEN 3Δ30/31) | NLT $log_{10}$ 2.5 PFU |
| Sucrose | 5% w/v |
| Glycine | 5% w/v |

TABLE 22D

| Dengue Monovalent Vaccine Composition SG4 | |
|---|---|
| Component | Quantity per dose of 0.5 ml |
| Dengue virus serotype 3 (rDEN 3Δ30/31) | NLT $log_{10}$ 2.5 PFU |
| Sucrose | 10% w/v |
| Glycine | 7% w/v |

TABLE 22E

| Dengue Monovalent Vaccine Composition SG5 | |
|---|---|
| Component | Quantity per dose of 0.5 ml |
| Dengue virus serotype 3 (rDEN 3Δ30/31) | NLT $log_{10}$ 2.5 PFU |
| Sucrose | 4.5% w/v |
| Glycine | 5% w/v |

TABLE 22F

| Dengue Monovalent Vaccine Composition SG6 | |
|---|---|
| Component | Quantity per dose of 0.5 ml |
| Dengue virus serotype 3 (rDEN 3Δ30/31) | NLT $log_{10}$ 2.5 PFU |
| Sucrose | 6% w/v |
| Glycine | 6% w/v |

TABLE 23A

| Dengue Monovalent Vaccine Composition SG1 | |
|---|---|
| Component | Quantity per dose of 0.5 ml |
| Dengue virus serotype 4 (rDEN 4Δ30) | NLT $log_{10}$ 2.5 PFU |
| Sucrose | 5% w/v |
| Glycine; | 3% w/v |

TABLE 23B

| Dengue Monovalent Vaccine Composition SG2 | |
|---|---|
| Component | Quantity per dose of 0.5ml |
| Dengue virus serotype 4 (rDEN 4Δ30) | NLT $log_{10}$ 2.5 PFU |
| Sucrose | 3% w/v |
| Glycine | 5% w/v |

TABLE 23C

| Dengue Monovalent Vaccine Composition SG3 | |
|---|---|
| Component | Quantity per dose of 0.5 ml |
| Dengue virus serotype 4 (rDEN 4Δ30) | NLT $log_{10}$ 2.5 PFU |
| Sucrose | 5% w/v |
| Glycine | 5% w/v |

TABLE 23D

| Dengue Monovalent Vaccine Composition SG4 | |
|---|---|
| Component | Quantity per dose of 0.5 ml |
| Dengue virus serotype 4 (rDEN 4Δ30) | NLT $log_{10}$ 2.5 PFU |
| Sucrose | 10% w/v |
| Glycine | 7% w/v |

TABLE 23E

| Dengue Monovalent Vaccine Composition SG5 | |
|---|---|
| Component | Quantity per dose of 0.5 ml |
| Dengue virus serotype 4 (rDEN 4Δ30) | NLT $log_{10}$ 2.5 PFU |
| Sucrose | 4.5% w/v |
| Glycine | 5% w/v |

TABLE 23F

| Dengue Monovalent Vaccine Composition SG6 | |
|---|---|
| Component | Quantity per dose of 0.5 ml |
| Dengue virus serotype 4 (rDEN 4Δ30) | NLT $log_{10}$ 2.5 PFU |
| Sucrose | 6% w/v |
| Glycine | 6% w/v |

TABLE 24

| Dengue Tetravalent Vaccine Composition SG1 | |
|---|---|
| Component | Quantity per dose of 0.5 ml |
| Dengue virus serotype 1 (rDEN 1Δ30) | NLT $log_{10}$ 2.5 PFU |
| Dengue virus serotype 2 (rDEN 2/4Δ30) | NLT $log_{10}$ 3.0 PFU |
| Dengue virus serotype 3 (rDEN 3Δ30/31) | NLT $log_{10}$ 2.5 PFU |
| Dengue virus serotype 4 (rDEN 4Δ30) | NLT $log_{10}$ 2.5 PFU |
| Sucrose | 5% w/v |
| Glycine | 3% w/v |

TABLE 25

| Dengue Tetravalent Vaccine Composition SG2 | |
|---|---|
| Component | Quantity per dose of 0.5 ml |
| Dengue virus serotype 1 (rDEN 1Δ30) | NLT $log_{10}$ 2.5 PFU |
| Dengue virus serotype 2 (rDEN 2/4Δ30) | NLT $log_{10}$ 3.0 PFU |
| Dengue virus serotype 3 (rDEN 3Δ30/31) | NLT $log_{10}$ 2.5 PFU |
| Dengue virus serotype 4 (rDEN 4Δ30) | NLT $log_{10}$ 2.5 PFU |
| Sucrose | 3% w/v |
| Glycine | 5% w/v |

TABLE 26

| Dengue Tetravalent Vaccine Composition SG3 | |
|---|---|
| Component | Quantity per dose of 0.5 ml |
| Dengue virus serotype 1 (rDEN 1Δ30) | NLT $log_{10}$ 2.5 PFU |
| Dengue virus serotype 2 (rDEN 2/4Δ30) | NLT $log_{10}$ 3.0 PFU |
| Dengue virus serotype 3 (rDEN 3Δ30/31) | NLT $log_{10}$ 2.5 PFU |
| Dengue virus serotype 4 (rDEN 4Δ30) | NLT $log_{10}$ 2.5 PFU |
| Sucrose | 5% w/v |
| Glycine | 5% w/v |

TABLE 27

| Dengue Tetravalent Vaccine Composition SG4 | |
|---|---|
| Component | Quantity per dose of 0.5 ml |
| Dengue virus serotype 1 (rDEN 1Δ30) | NLT $log_{10}$ 2.5 PFU |
| Dengue virus serotype 2 (rDEN 2/4Δ30) | NLT $log_{10}$ 3.0 PFU |
| Dengue virus serotype 3 (rDEN 3Δ30/31) | NLT $log_{10}$ 2.5 PFU |
| Dengue virus serotype 4 (rDEN 4Δ30) | NLT $log_{10}$ 2.5 PFU |
| Sucrose | 10% w/v |
| Glycine | 7% w/v |

TABLE 28

| Dengue Tetravalent Vaccine Composition SG5 | |
|---|---|
| Component | Quantity per dose of 0.5 ml |
| Dengue virus serotype 1 (rDEN 1Δ30) | NLT $log_{10}$ 2.5 PFU |
| Dengue virus serotype 2 (rDEN 2/4Δ30) | NLT $log_{10}$ 3.0 PFU |
| Dengue virus serotype 3 (rDEN 3Δ30/31) | NLT $log_{10}$ 2.5 PFU |
| Dengue virus serotype 4 (rDEN 4Δ30) | NLT $log_{10}$ 2.5 PFU |
| Sucrose | 4.5% w/v |
| Glycine | 5% w/v |

TABLE 29

| Dengue Tetravalent Vaccine Composition SG6 | |
|---|---|
| Component | Quantity per dose of 0.5 ml |
| Dengue virus serotype 1 (rDEN 1Δ30) | NLT $log_{10}$ 2.5 PFU |
| Dengue virus serotype 2 (rDEN 2/4Δ30) | NLT $log_{10}$ 3.0 PFU |
| Dengue virus serotype 3 (rDEN 3Δ30/31) | NLT $log_{10}$ 2.5 PFU |
| Dengue virus serotype 4 (rDEN 4Δ30) | NLT $log_{10}$ 2.5 PFU |
| Sucrose | 6% w/v |
| Glycine | 6% w/v |

TABLE 30

DEN 1 Titer $Log_{10}$ pfu/ml post lyophilization

| Storage time | SG1 | SG2 | SG3 | SG4 | SG5 | SG6 |
|---|---|---|---|---|---|---|
| 0 | 7.105 | 7.024 | 7.217 | 7.185 | 7.060 | 6.994 |
| 1 | 7.020 | 7.051 | 7.300 | 7.242 | 7.021 | 6.950 |
| 3 | 6.898 | 6.917 | 7.152 | 7.082 | 6.935 | 6.886 |
| 5 | 6.925 | 6.720 | 6.954 | 6.981 | 6.724 | 6.817 |
| 7 | 6.700 | 6.510 | 6.872 | 6.732 | 6.600 | 6.746 |
| 14 | 6.346 | 6.180 | 6.585 | 6.500 | 6.312 | 6.395 |

TABLE 31

Refer FIG. 13: DEN-1 titer $Log_{10}$ pfu/ml post lyophilization
DEN 2 Titer $Log_{10}$ pfu/ml post lyophilization

| Storage time | SG1 | SG2 | SG3 | SG4 | SG5 | SG6 |
|---|---|---|---|---|---|---|
| 0 | 6.775 | 6.821 | 6.824 | 6.780 | 6.900 | 6.772 |
| 1 | 6.650 | 6.760 | 6.797 | 6.802 | 6.855 | 6.780 |
| 3 | 6.684 | 6.617 | 6.712 | 6.689 | 6.723 | 6.665 |
| 5 | 6.521 | 6.588 | 6.610 | 6.584 | 6.692 | 6.610 |
| 7 | 6.246 | 6.405 | 6.482 | 6.410 | 6.536 | 6.538 |
| 14 | 6.060 | 6.144 | 6.227 | 6.197 | 6.272 | 6.294 |

TABLE 32

Refer FIG. 14: DEN-2 titer $Log_{10}$ pfu/ml post lyophilization
DEN 3Titer $Log_{10}$ pfu/ml post lyophilization

| Storage time | SG1 | SG2 | SG3 | SG4 | SG5 | SG6 |
|---|---|---|---|---|---|---|
| 0 | 5.929 | 5.864 | 5.882 | 5.877 | 5.765 | 5.800 |
| 1 | 5.788 | 5.712 | 5.800 | 5.762 | 5.692 | 5.728 |
| 3 | 5.621 | 5.644 | 5.725 | 5.688 | 5.566 | 5.610 |
| 5 | 5.546 | 5.571 | 5.622 | 5.621 | 5.487 | 5.543 |
| 7 | 5.440 | 5.473 | 5.496 | 5.492 | 5.351 | 5.414 |
| 14 | 5.132 | 5.082 | 5.184 | 5.131 | 5.139 | 5.220 |

TABLE 33

Refer FIG. 15: DEN-3 titer $Log_{10}$ pfu/ml post lyophilization
DEN 4Titer $Log_{10}$ pfu/ml post lyohilization

| Storage time | SG1 | SG2 | SG3 | SG4 | SG5 | SG6 |
|---|---|---|---|---|---|---|
| 0 | 7.429 | 7.441 | 7.512 | 7.464 | 7.500 | 7.471 |
| 1 | 7.366 | 7.400 | 7.504 | 7.471 | 7.432 | 7.388 |
| 3 | 7.302 | 7.343 | 7.438 | 7.402 | 7.386 | 7.295 |
| 5 | 7.210 | 7.219 | 7.393 | 7.330 | 7.277 | 7.197 |
| 7 | 7.157 | 7.134 | 7.268 | 7.225 | 7.150 | 7.065 |
| 14 | 6.809 | 6.792 | 7.021 | 6.96 | 6.880 | 6.782 |

Refer FIG. 16: DEN-4 titer $Log_{10}$ pfu/ml post lyophilization

Aforementioned thermal stability results for lyophilized monovalent formulations containing varying concentrations of sucrose and glycine stabilizers; indicate that the concentration of both sucrose & glycine plays major role in maintaining the virus infectivity titer.

Comparatively more variation in virus titers was observed with SG1 & SG2 formulations. No significant difference was observed with SG3, SG4, SG 5, SG 6, formulations in all four serotypes. However, SG3 i.e. 5% Sucrose & 5% Glycine formulation was the choice of stabilizer composition for further batches.

Example 7

Stability Data of Dengue Tetravalent Vaccine, Live Attenuated (Recombinant, Lyophilized)

Dengue Tetravalent Vaccine (DTV)(live, attenuated, Recombinant) having a combination of serotypes (DEN-1, DEN 2, DEN-3, DEN-4) stabilized using sucrose-glycine (SG) composition as enclosed in Example 6 and further lyophilized according to example 5 in 3 ml tubular USP type-1 glass vials. Container closure system consists of bromobutyl rubber stoppers and flip-off aluminium and plastic caps seals.

The stability and quality of SG-stabilized vaccine was evaluated in the above-said container closure system for following studies in line with ICH requirement to support the expiry period of DP.

Stability indicating parameters for long-term/real time stability studies were following:

1. Virus titers of each serotype
2. pH
3. Moisture content

1. Dengue Tetravalent Vaccine Stability Data at 2-8° C. Up to 12 Months Post Lyophilization:

TABLE 34A

| DEN-1 titer $Log_{10}$ pfu/0.5 ml data post lyophilization at 2-8° C. upto 12 months | | | | | | | |
|---|---|---|---|---|---|---|---|
| No. | 0 | 1 | 2 | 3 | 6 | 9 | 12 |
| Batch4 | 4.62 | 4.43 | 4.29 | 4.44 | 4.61 | 4.4 | 4.65 |
| Batch5 | 5.17 | 4.8 | 4.69 | 4.85 | 4.83 | 4.67 | 4.59 |
| Batch6 | 4.88 | 4.57 | 4.57 | 4.7 | 4.55 | 4.62 | 4.59 |

Refer FIG. 17A: DEN-1 titer $Log_{10}$ pfu/0.5 ml data post lyophilization at 2-8° C. upto 12 months

TABLE 34B

| DEN-2 titer $Log_{10}$ pfu/0.5 ml data post lyophilization at 2-8° C. upto 12 months | | | | | | | |
|---|---|---|---|---|---|---|---|
| No. | 0 | 1 | 2 | 3 | 6 | 9 | 12 |
| Batch4 | 5.22 | 5.06 | 4.93 | 4.92 | 5.14 | 4.85 | 4.88 |
| Batch5 | 5.03 | 4.79 | 4.82 | 4.81 | 4.80 | 4.78 | 4.38 |
| Batch6 | 5.01 | 4.93 | 4.85 | 4.86 | 4.88 | 4.63 | 4.24 |

Refer FIG. 17B: DEN-2 titer $Log_{10}$ pfu/0.5 ml data post lyophilization at 2-8° C. upto 12 months

TABLE 34C

| DEN-3 titer $Log_{10}$ pfu/0.5 ml data post lyophilization at 2-8° C. upto 12 months | | | | | | | |
|---|---|---|---|---|---|---|---|
| No. | 0 | 1 | 2 | 3 | 6 | 9 | 12 |
| Batch4 | 4.62 | 4.31 | 4.25 | 4.38 | 4.56 | 4.33 | 4.52 |
| Batch5 | 5.30 | 4.85 | 4.51 | 5.05 | 4.96 | 4.69 | 4.45 |
| Batch6 | 5.00 | 4.57 | 4.52 | 4.69 | 4.59 | 4.54 | 4.05 |

Refer FIG. 17C: DEN-3 titer $Log_{10}$ pfu/0.5 ml data post lyophilization at 2-8° C. upto 12 months

TABLE 34D

| DEN-4 titer $Log_{10}$ pfu/0.5 ml data post lyophilization at 2-8° C. upto 12 months | | | | | | | |
|---|---|---|---|---|---|---|---|
| No. | 0 | 1 | 2 | 3 | 6 | 9 | 12 |
| Batch4 | 5.28 | 5.09 | 4.89 | 4.92 | 5.06 | 4.91 | 4.90 |
| Batch5 | 5.27 | 5.02 | 4.93 | 4.9 | 5.04 | 4.84 | 4.38 |
| Batch6 | 4.78 | 4.34 | 4.53 | 4.49 | 4.66 | 4.36 | 3.97 |

Refer FIG. 17D: DEN-4 titer $Log_{10}$ pfu/0.5 ml data post lyophilization at 2-80 C upto 12 months pH and moisture content was estimated at 2-8° C. upto 12 months. pH remained within the range of 7.6 to 7.8 (FIG. 18). Residual moisture content remained below than 3.0% w/w up to 12 months storage, (FIG. 19).

2. Dengue Tetravalent Vaccine Stability Data at 25° C.±2° C. and 60%±5% Relative Humidity Upto 6 Months Post Lyophilization:

TABLE 35A

| DEN-1 titer $Log_{10}$ pfu/0.5 ml data post lyophilization at 25° C. up to 6 months | | | | | |
|---|---|---|---|---|---|
| No. | 0 | 1 | 2 | 3 | 6 |
| Batch 4 | 4.32 | 4.19 | 4.44 | 4.47 | 4.39 |
| Batch 5 | 4.87 | 4.82 | 4.87 | 4.81 | 4.74 |
| Batch 6 | 4.57 | 4.70 | 4.77 | 4.62 | 4.61 |

Refer FIG. 20A: DEN-1 titer $Log_{10}$ pfu/0.5 ml data post lyophilization at 25° C.±2° C. upto 6 months

TABLE 35B

| DEN-2 titer $Log_{10}$ pfu/0.5 ml data post lyophilization at 25° C. up to 6 months | | | | | |
|---|---|---|---|---|---|
| No. | 0 | 1 | 2 | 3 | 6 |
| Batch 4 | 4.92 | 4.95 | 5.11 | 5.10 | 4.87 |
| Batch 5 | 4.73 | 4.69 | 4.89 | 4.91 | 4.74 |
| Batch 6 | 4.71 | 4.72 | 4.85 | 4.81 | 4.67 |

Refer FIG. 20B: DEN-2 titer $Log_{10}$ pfu/0.5 ml data post lyophilization at 25° C.±2° C. upto 6 months

TABLE 35C

| DEN-3 titer $Log_{10}$ pfu/0.5 ml data post lyophilization at 25° C. up to 6 months | | | | | |
|---|---|---|---|---|---|
| No. | 0 | 1 | 2 | 3 | 6 |
| Batch 4 | 4.32 | 4.36 | 4.35 | 4.37 | 4.40 |
| Batch 5 | 4.99 | 4.86 | 4.91 | 5.03 | 4.85 |
| Batch 6 | 4.69 | 4.66 | 4.76 | 4.84 | 4.65 |

Refer FIG. 20C: DEN-3 titer $Log_{10}$ pfu/0.5 ml data post lyophilization at 25° C.±2° C. upto 6 months

TABLE 35D

| DEN-4 titer $Log_{10}$ pfu/0.5 ml data post lyophilization at 25° C. up to 6 months | | | | | |
|---|---|---|---|---|---|
| No. | 0 | 1 | 2 | 3 | 6 |
| Batch 4 | 4.98 | 4.95 | 5.11 | 5.08 | 4.91 |
| Batch 5 | 4.97 | 4.86 | 5.08 | 5.03 | 4.89 |
| Batch 6 | 4.48 | 4.43 | 4.57 | 4.39 | 4.36 |

Refer FIG. 20D: DEN-4 titer $Log_{10}$ pfu/0.5 ml data post lyophilization at 25° C.±2° C. upto 6 months The pH and moisture content was estimated on initial and final time point at 25° C.±2° C. upto 6 months (6 months post exposure). No change in pH occurred on storage at accelerated conditions for 6 months compared to initial values ($p<0.001$); Mean±3SD shifted from 7.60-7.79 to 7.54-7.71 (FIG. 21). Residual moisture content remained within upper limit of 3% w/w, Meant±3SD of 1.845-2.774% w/w after 6 months post storage (FIG. 22).

3. Dengue Tetravalent Vaccine Stability Data at 37° C.±1° C. Upto 7 Days Post Lyophilization:

Batches were exposed to 37° C.±1° C. for 7 days. Virus serotypes (DEN1-4) were titrated and loss in titers was calculated. Loss in titers was consistent in all batches. Average $Log_{10}$ loss in virus titers and standard deviation of Dengue 1 to Dengue 4 serotypes in lyophilized DTV were 0.604±0.117, 0.607±0.066, 0.548±0.130, 0.684±0.109 respectively (FIG. 23).

TABLE 36

| Dengue Tetravalent Vaccine Stability data Post lyophilization at 37° C. ± 1° C. up to 7 days | | | | |
|---|---|---|---|---|
| B.No. | DEN1 | DEN2 | DEN3 | DEN4 |
| Batch 1 | 0.60 | 0.68 | 0.60 | 0.68 |
| Batch 2 | 0.68 | 0.61 | 0.69 | 0.62 |
| Batch 3 | 0.50 | 0.54 | 0.41 | 0.61 |
| Batch 4 | 0.67 | 0.67 | 0.52 | 0.76 |
| Batch 5 | 0.69 | 0.50 | 0.65 | 0.69 |
| Batch 6 | 0.71 | 0.65 | 0.63 | 0.87 |

Refer FIG. 23: Dengue Tetravalent Vaccine Stability data at 37° C.±1° C. upto 7 days post lyophilization 4. Dengue Tetravalent Vaccine Stability Data at 42° C.±1° C. Upto 7 Days Post Lyophilization:

Stability of Dengue Tetravalent Vaccine (DTV) (live, attenuated) was evaluated on a representative batch. Lyophilized finished product vials were exposed to thermal stress condition at 42° C. for 7 days. Each virus serotype (DEN 1-4) was titrated at the end of exposure period, compared with the initial titer and loss in titers was calculated.

(Refer FIG. 24)

TABLE 37

| Dengue Tetravalent Vaccine Stability data Post lyophilization at 42° C. ± 1° C. up to 7 days | | | | |
|---|---|---|---|---|
| Days post | Logio loss in virus titers of DTV (pfu/0.5 ml) | | | |
| exposure | DEN1 | DEN2 | DEN3 | DEN4 |
| 0 day | 4.41 | 4.43 | 4.26 | 4.06 |
| 7 day | 3.91 | 3.81 | 3.83 | 3.42 |
| Loss in titer | 0.50 | 0.62 | 0.43 | 0.64 |

5. Dengue Tetravalent Vaccine Stability Data at 55° C.±1° C. Upto 2 Days Post Lyophilization:

Stability of Dengue Tetravalent Vaccine (DTV) (live, attenuated) was evaluated on a representative batch. Lyophilized finished product vials were exposed to thermal stress condition at 55° C. for 2 days. Each virus serotype (DEN1-4) was titrated at the end of exposure period, compared with the initial titer and loss in titers was calculated.

While the present invention has been described with respect to certain preferred embodiments, it will be apparent to those skilled in the art that various changes and modifications may be made without departing from the scope of the invention as defined in the following claims.

We claim:

1. An immunogenic composition comprising:

a) one or more live attenuated dengue (DEN) viruses;

b) sucrose in an amount of about 3 to 6% (w/v); and c) glycine in an amount of about 3 to 6% (w/v);

wherein, the composition is freeze dried and the reconstituted composition preserves the desired characteristics of a virus, including virus viability, immunogenicity and stability;

wherein the composition is devoid of preservatives, polymers and surfactants; and wherein the composition is devoid of an excipient or stabilizer of animal origin or an excipient or stabilizer which contains an animal component.

2. The immunogenic composition as claimed in claim 1, wherein the one or more live attenuated dengue (DEN) viruses, comprises a plurality of live attenuated dengue (DEN) viruses of different serotypes selected from a group consisting of DEN-1, DEN-2, DEN-3 and DEN-4.

3. The immunogenic composition as claimed in claim 2, wherein the live attenuated dengue (DEN) virus is tetravalent comprising dengue virus serotypes DEN-1, DEN-2, DEN-3 and DEN-4.

4. The immunogenic composition as claimed in claim 3, wherein the live attenuated dengue (DEN) virus is recombinant dengue viruses and/or a chimeric dengue viruses comprising a first nucleotide sequence encoding at least one structural protein from a first dengue virus and a second nucleotide sequence encoding non-structural proteins from a second dengue virus.

5. The immunogenic composition as claimed in claim 4, wherein said live attenuated dengue virus serotypes DEN-1, DEN-2, DEN-3 and DEN-4 carry 30 nucleotide deletion denoted Δ 30 mutation and/or carry 31 nucleotide deletion denoted Δ 31 mutation in the 3' untranslated region of dengue virus genome.

6. The immunogenic composition as claimed in claim 5, wherein said live attenuated dengue virus serotypes DEN-1, DEN-2, DEN-3 and DEN-4 have a phenotype which is temperature sensitive in Vero cells or a human liver cell line HuH-7.

7. The immunogenic composition as claimed in claim 1, wherein the composition is lyophilized (freeze-dried).

8. The immunogenic composition as claimed in claim 7, wherein the lyophilized composition is reconstituted with an aqueous solution selected from saline and WFI (water for injection), and wherein the final pH of the reconstituted immunogenic composition is 7-8.

9. The immunogenic composition as claimed in claim 1, wherein the dengue virus is present at a dose of not less than 2.5 log 10 PFU per 0.5 ml.

10. The immunogenic composition as claimed in claim 1, comprising:

a) Dengue virus serotype 1 (rDEN 1Δ30), b) Dengue virus serotype 2 (rDEN 2/4Δ30), c) Dengue virus serotype 3 (rDEN 3Δ30/31), d) Dengue virus serotype 4 (rDEN 4Δ30), e) Sucrose 3 to 6% (w/v), and f) Glycine 3 to 6% (w/v).

11. The immunogenic composition as claimed in claim 10, comprising:

a) Dengue virus serotype 1 (rDEN 1Δ30), b) Dengue virus serotype 2 (rDEN 2/4Δ30), c) Dengue virus serotype 3 (rDEN 3Δ30/31), d) Dengue virus serotype 4 (rDEN 4Δ30), e) Sucrose 4 to 5% (w/v), and f) Glycine 4 to 5% (w/v).

12. The immunogenic composition as claimed in claim 10, comprising:

a) Dengue virus serotype 1 (rDEN 1Δ30), NLT 2.5 $\log_{10}$ PFU per 0.5 ml, b) Dengue virus serotype 2 (rDEN 2/4Δ30), NLT 2.5 $\log_{10}$ PFU per 0.5 ml, c) Dengue virus serotype 3 (rDEN 3Δ30/31), NLT 2.5 $\log_{10}$ PFU per 0.5 ml, d) Dengue virus serotype 4 (rDEN 4Δ30), NLT 2.5 $\log_{10}$ PFU per 0.5 ml, e) Sucrose about 5% (w/v), and f) Glycine about 5% (w/v).

13. The immunogenic composition as claimed in claim 10, comprising:

a) Dengue virus serotype 1 (rDEN 1Δ30), NLT 2.5 $log_{10}$ PFU per 0.5 ml, b) Dengue virus serotype 2 (rDEN 2/4Δ30), NLT 2.5 $log_{10}$ PFU per 0.5 ml, c) Dengue virus serotype 3 (rDEN 3Δ30/31), NLT 2.5 $log_{10}$ PFU per 0.5 ml, d) Dengue virus serotype 4 (rDEN 4Δ30), NLT 2.5 $log_{10}$ PFU per 0.5 ml, e) Sucrose about 4.5% (w/v), and f) Glycine about 5% (w/v).

14. The immunogenic composition as claimed in claim 10, comprising:

a) Dengue virus serotype 1 (rDEN 1Δ30), NLT 2.5 $log_{10}$ PFU per 0.5 ml, b) Dengue virus serotype 2 (rDEN 2/4Δ30), NLT 2.5 $log_{10}$ PFU per 0.5 ml, c) Dengue virus serotype 3 (rDEN 3Δ30/31), NLT 2.5 $log_{10}$ PFU per 0.5 ml, d) Dengue virus serotype 4 (rDEN 4Δ30), NLT 2.5 $log_{10}$ PFU per 0.5 ml, e) Sucrose about 6% (w/v), and f) Glycine about 6% (w/v).

15. A method of manufacturing an immunogenic composition comprising:

multiple harvesting of supernatant comprising at least one serotype of dengue virus in minimum essential medium (MEM) additionally containing dextrose, L-glutamine and sodium bicarbonate wherein the multiple harvesting is carried out from a single batch;

filtering the viral harvest by direct flow filtration (DFF) through at least one clarification filter having a pore size of between 6 micrometers to 0.45 micrometers;

testing the viral harvest with a benzonase having a concentration in the range of 0.5 units/ml to 5 units/ml at 34±1° C. for at least 2 hours;

concentrating the viral harvest by tangential flow filtration (TFF) using membrane with a molecular weight cut off (MWCO) of 100 kDa;

stabilizing the viral harvest with a stabilizing agent comprising sucrose at a concentration of 3 to 6% (w/v) and glycine at a concentration of 3 to 6% (w/v) to form a stabilized viral harvest;

sterilizing the stabilized viral harvest by DFF through at least one clarification filter having a pore size of between 0.8 micrometers to 0.2 micrometers to form a sterilized viral harvest of purified virus, wherein the overall recovery of purified viruses is at least 50%; and optionally freeze drying the sterilized viral harvest comprising the step of freezing, primary drying and secondary drying, wherein a. the freezing step comprises freezing at −45° C. for 690 minutes to 930 minutes, b. the primary drying step comprises ramping at +0.5° C./minute to 1° C./minute to achieve a shelf temperature of −25° C. holding for 1800 minutes to 1980 minutes, and c. the secondary drying step comprises ramping at +0.5° C./minute to 1.0° C./minute to achieve a shelf temperature of +25° C. holding for 420 minutes to 540 minutes.

16. The method as claimed in claim 15, wherein the viral harvest is treated with benzonase having a concentration of 1.25 units/ml.

17. The method as claimed in claim 15, wherein the viral harvest is subjected to tangential flow filtration (TFF) resulting in at least 10× concentration of the viral harvest.

18. The method as claimed in claim 15, wherein the freezing step comprises freezing at about −45° C. for about 60 minutes.

19. The method as claimed in claim 15, wherein the primary drying step comprises ramping at about +0.5° C./minute to 1.0° C./minute to achieve the shelf temperature of about −32° C., holding for about 600 minutes to 1800 minutes.

20. The method as claimed in claim 15, wherein the secondary drying step comprises ramping at about +0.5° C./minute to 1.0° C./minute to achieve the shelf temperature of about +25° C., holding for about 360 minutes to 600 minutes.

21. A kit comprising:

a first container containing a lyophilized immunogenic composition, said composition comprising:

i. one or more live attenuated dengue (DEN) virus;

ii. sucrose 3 to 6% (w/v); and iii. glycine 3 to 6% (w/v); and a second container containing an aqueous solution selected from saline or WFI (water for injection) for reconstitution of the lyophilized (freeze-dried) immunogenic composition;

wherein the composition is devoid of preservatives, polymers and surfactants; and wherein the composition is devoid of an excipient or stabilizer of animal origin or an excipient or stabilizer which contains an animal component.

* * * * *